(12) United States Patent
Okada

(10) Patent No.: US 11,504,143 B2
(45) Date of Patent: Nov. 22, 2022

(54) ENDOSCOPE TREATMENT TOOL

(71) Applicant: OLYMPUS CORPORATION, Tokyo (JP)

(72) Inventor: Tsutomu Okada, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 50 days.

(21) Appl. No.: 17/131,880

(22) Filed: Dec. 23, 2020

(65) Prior Publication Data

US 2021/0113226 A1 Apr. 22, 2021

Related U.S. Application Data

(63) Continuation of application No. PCT/JP2018/024582, filed on Jun. 28, 2018.

(51) Int. Cl.
*A61B 17/221* (2006.01)
*A61B 17/00* (2006.01)

(52) U.S. Cl.
CPC ...... *A61B 17/221* (2013.01); *A61B 17/00234* (2013.01); *A61B 2017/00296* (2013.01); *A61B 2017/2217* (2013.01)

(58) Field of Classification Search
CPC .......... A61B 17/00234; A61B 17/0057; A61B 17/221; A61B 2017/00296;
(Continued)

(56) References Cited

U.S. PATENT DOCUMENTS 4,691,705 A * 9/1987 Okada ............... A61B 17/221
606/127
4,741,335 A 5/1988 Okada
(Continued)

FOREIGN PATENT DOCUMENTS

EP 0152032 A2 8/1985
EP 3 081 177 A1 10/2016
(Continued)

OTHER PUBLICATIONS

International Search Report dated Mar. 19, 2019 received in PCT/JP2018/047830.
(Continued)

*Primary Examiner* — Kathleen S Holwerda
*Assistant Examiner* — Kankindi Rwego
(74) *Attorney, Agent, or Firm* — Scully, Scott, Murphy & Presser, P.C.

(57) ABSTRACT

An endoscope treatment tool includes: a sheath; an operating wire in the sheath; a gripping portion provided at a distal end of the operating wire and having one or more wires; a tip attached to a distal end of the sheath; and a resin member disposed at a position adjacent to the tip on a radially inner or outer side thereof, wherein the tip includes clearance grooves extending toward a proximal end of the tip from a distal end of the tip, passing therethrough from an inner circumferential surface of the tip to an outer circumferential surface of the tip, and having sizes enabling the wires to pass therethrough, and at least proximal-end sides of the grooves overlap with the member in a radial direction of the tip and a distal end of the member is disposed farther on a distal-end side than proximal ends of the grooves are.

18 Claims, 23 Drawing Sheets

(58) Field of Classification Search
CPC .. A61B 2017/0036; A61B 2017/00818; A61B 2017/2212; A61B 2017/2217; A61B 1/0008; A61B 1/00085; A61B 1/00098; A61B 1/00101; A61M 25/00; A61M 25/0067; A61M 25/0082; A61F 2/00; A61F 2/01; A61F 2/011; A61F 2/013; A61F 2/24; A61F 2/2427; A61F 2/243; A61F 2/2433; A61F 2/2436; A61F 2/95; A61F 2/9522; A61F 2002/015; A61F 2002/016; A61F 2002/018
USPC .......................................................... 606/127
See application file for complete search history.

(56) References Cited

U.S. PATENT DOCUMENTS

| | | | |
|---|---|---|---|
| 6,013,086 A * | 1/2000 | Ouchi | A61B 17/221 606/127 |
| 6,077,274 A | 6/2000 | Ouchi et al. | |
| 6,187,017 B1 | 2/2001 | Gregory, Jr. | |
| 6,468,285 B1 | 10/2002 | Hsu et al. | |
| 2002/0091394 A1 | 7/2002 | Reynolds et al. | |
| 2004/0116941 A1 | 6/2004 | Reynolds et al. | |
| 2010/0106164 A1 | 4/2010 | Reynolds et al. | |
| 2016/0192957 A1 | 7/2016 | Okada | |
| 2017/0156745 A1 | 6/2017 | Okada | |

FOREIGN PATENT DOCUMENTS

| | | |
|---|---|---|
| EP | 3318205 A1 | 5/2018 |
| JP | S56-109705 U | 8/1981 |
| JP | S60-096241 A | 5/1985 |
| JP | S60-242848 A | 12/1985 |
| JP | S62-014811 Y2 | 4/1987 |
| JP | S62-014812 Y2 | 4/1987 |
| JP | S62-041724 B2 | 9/1987 |
| JP | S63-020140 B2 | 4/1988 |
| JP | H03-231654 A | 10/1991 |
| JP | H05-000116 U | 1/1993 |
| JP | H06-133978 A | 5/1994 |
| JP | H09-168543 A | 6/1997 |
| JP | H11-047141 A | 2/1999 |
| JP | H11-099157 A | 4/1999 |
| JP | 2000-126193 A | 5/2000 |
| JP | 2002-017739 A | 1/2002 |
| JP | 2004-516880 A | 6/2004 |
| JP | 2005-021195 A | 1/2005 |
| JP | 2006-314715 A | 11/2006 |
| JP | 2013-022386 A | 2/2013 |
| JP | 2015-116399 A | 6/2015 |
| WO | 02/053037 A2 | 7/2002 |
| WO | 2015/087952 A1 | 6/2015 |
| WO | 2017/002438 A1 | 1/2017 |

OTHER PUBLICATIONS

Written Opinion of the International Search Authority dated Aug. 28, 2018 received in PCT/JP2018/024582.
Zeon Medical Inc., Zemex Crusher Catheter M_Product information, retrieved from the internet in Aug. 2020, URL:https://www.zeonmedical.co.jp/product/digestive/crusher_catheter/index_01.html, together with partial English translation.
Boston Scientific Corporation, StoneSmash Product information, retrieved from the internet in Aug. 2020, URL:https://www.bostonscientific.com/jp-JP/products/basket/StoneSmash.html, together with partial English translation.
International Search Report dated Aug. 28, 2018 issued in International Application No. PCT/JP2018/024582, together with partial English translation.

* cited by examiner

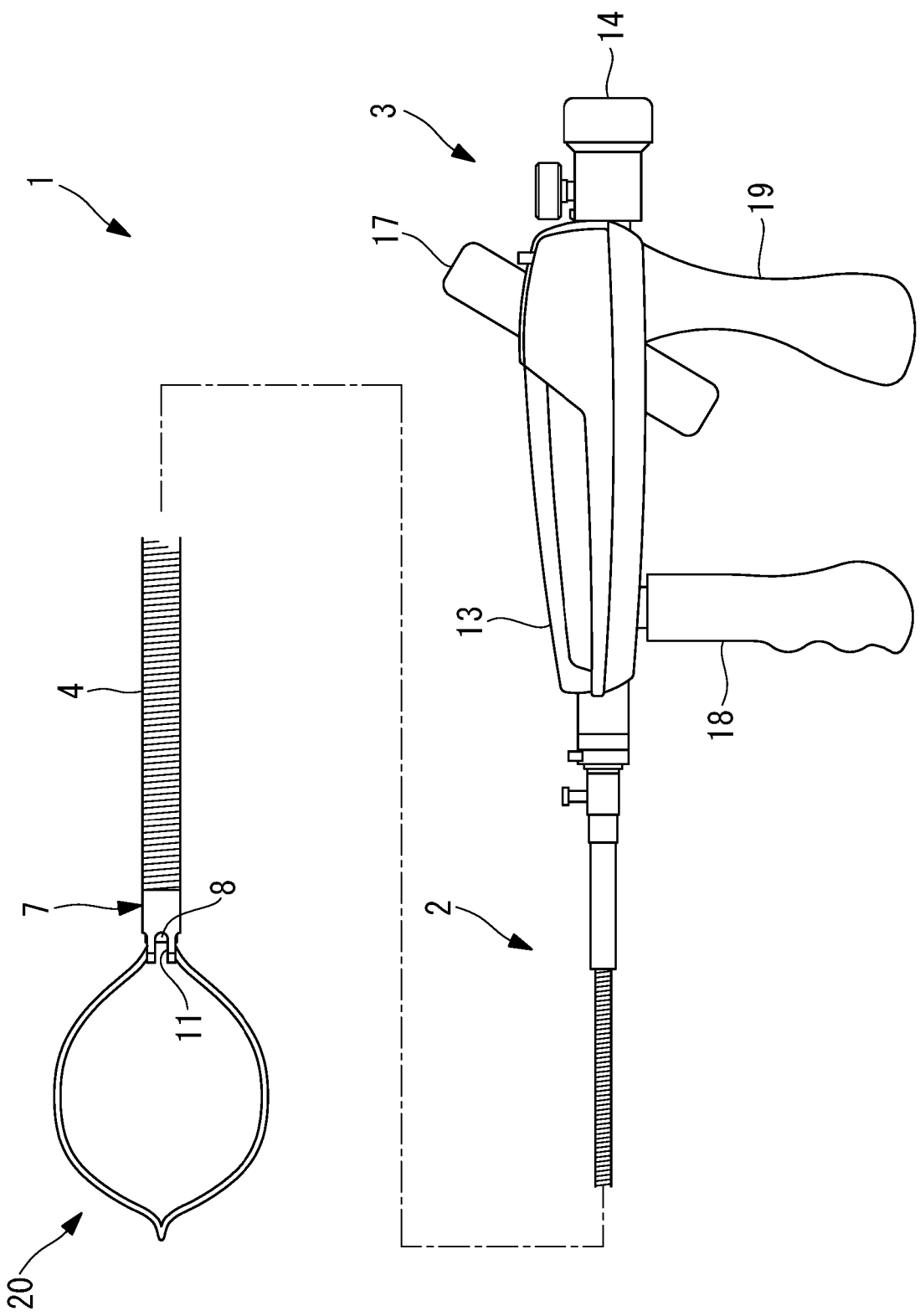

ENDOSCOPE TREATMENT TOOL

CROSS-REFERENCE TO RELATED APPLICATIONS

This is a continuation of International Application PCT/JP2018/024582 which is hereby incorporated by reference herein in its entirety.

TECHNICAL FIELD

The present invention relates to an endoscope treatment tool.

BACKGROUND ART

There is a known endoscope treatment tool that is inserted into a channel of an endoscope and endoscopically performs treatment in the case in which a calculus occurring in an organ, such as the bile duct, the bladder, or the like, is to be crushed (for example, see Patent Literature 1).

In addition, in the case in which a calculus captured in a basket wire is crushed in an endoscope treatment tool in which the basket wire is made to protrude from an inner hole of a short-tube-like rigid distal-end tip secured to a distal end of a flexible tube, there is a known endoscope treatment tool provided with, at a distal-end tip thereof, a clearance groove in which a basket wire is retracted in order to solve the problem in which transmission of force to the basket wire is prevented as a result of the basket wire being caught between the distal-end tip and the calculus (for example, see Patent Literature 2).

CITATION LIST

Patent Literatures

{PTL 1} Japanese Unexamined Patent Application, Publication No. 2006-314715
{PTL 2} Japanese Examined Utility Model Application, Publication No. Sho 62-41724

SUMMARY OF INVENTION

An aspect of the present invention is an endoscope treatment tool including: a tubular sheath having a longitudinal axis; an operating wire that is disposed in an interior of the sheath so as to be movable along the longitudinal axis; a gripping portion that is provided at a distal end of the operating wire and that has one or more wires for gripping a calculus; a cylindrical metal distal-end tip that is attached to a distal end of the sheath; and a resin member that is disposed at a position adjacent to the distal-end tip on a radially inner side or outer side thereof, wherein the distal-end tip is provided with clearance grooves that extend toward a proximal end of the distal-end tip from a distal end of the distal-end tip, that pass therethrough from an inner circumferential surface of the distal-end tip to an outer circumferential surface of the distal-end tip, and that have sizes enabling the wires of the gripping portion to pass therethrough, and at least proximal-end sides of the clearance grooves overlap with the resin member in a radial direction of the distal-end tip and a distal end of the resin member is disposed farther on a distal-end side than proximal ends of the clearance grooves are.

Another aspect of the present invention is an endoscope treatment tool including: a tubular sheath having a longitudinal axis; an operating wire that is disposed in an interior of the sheath so as to be movable along the longitudinal axis; a gripping portion that is provided at a distal end of the operating wire and that has one or more wires for gripping a calculus; and clearance grooves that extend toward a proximal end of the sheath from a distal end of the sheath, that pass therethrough from an inner circumferential surface of the sheath to an outer circumferential surface of the sheath, and that have sizes enabling the wires of the gripping portion to pass therethrough, wherein a resin member that is disposed at a position adjacent to the sheath on a radially inner side or outer side thereof is provided, and a distal end of the resin member is disposed farther on a distal-end side than the distal end of the sheath is.

Further another aspect of the present invention is an endoscope treatment tool including: a sheath having a longitudinal axis; an operating wire that is disposed in an interior of the sheath so as to be movable along the longitudinal axis; a gripping portion that is provided at a distal end of the operating wire and that has one or more wires for gripping a calculus; and a resin member that receives the gripping portion when the operating wire is pulled.

BRIEF DESCRIPTION OF DRAWINGS

FIG. 25 is an overall configuration diagram showing a modification of a gripping portion in FIG. 1.

DESCRIPTION OF EMBODIMENTS

An endoscope treatment tool 1 according to a first embodiment of the present invention will be described below with reference to the drawings.

Figure 1:
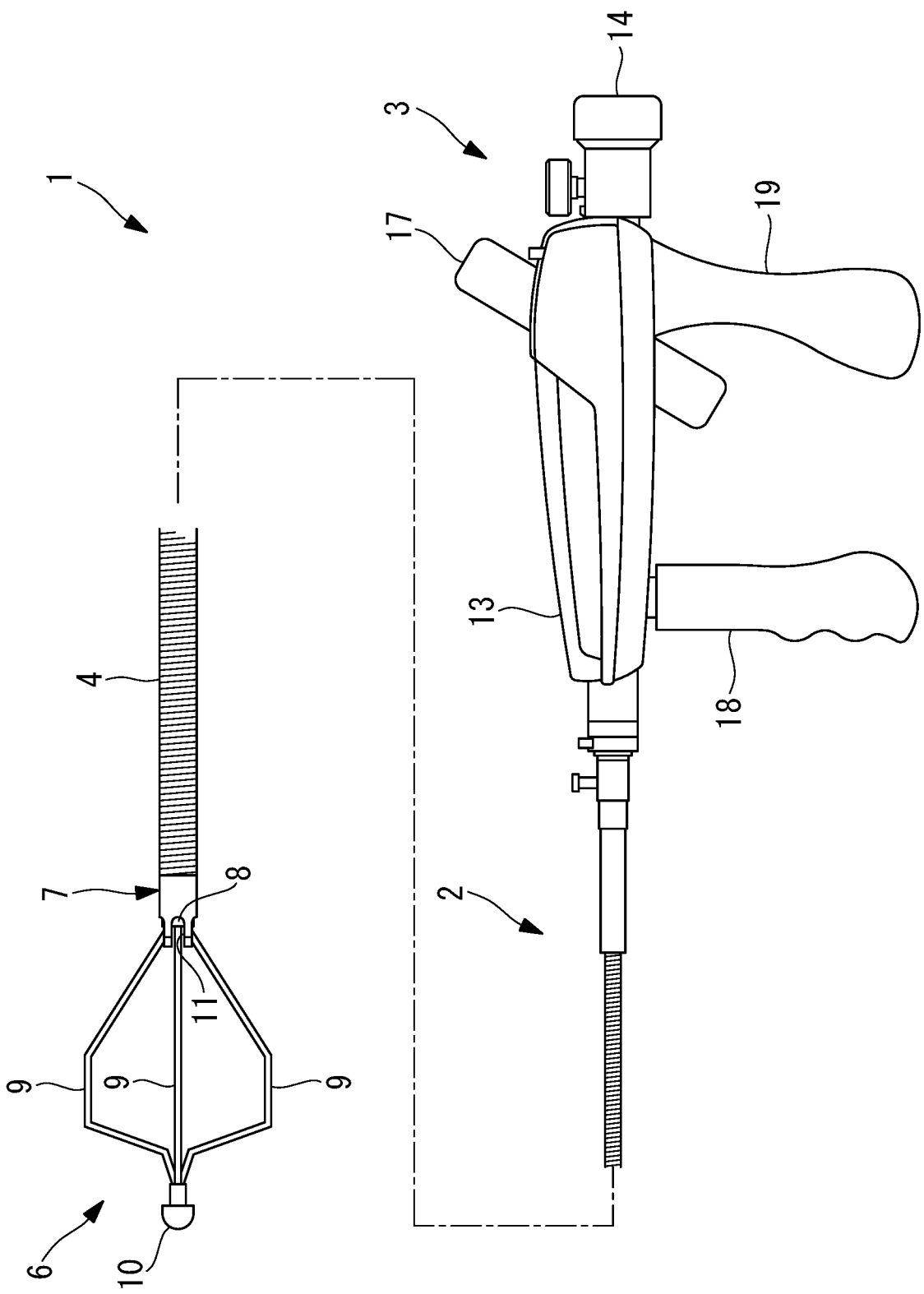
FIG. 1 is an overall configuration diagram showing an endoscope treatment tool according to a first embodiment of the present invention.

The endoscope treatment tool 1 according to this embodiment will be described by way of a calculus crushing device including a basket that captures a calculus X in a patient. As shown in FIG. 1, the endoscope treatment tool 1 according to this embodiment includes an elongated insertion portion 2 and an operating portion 3 that is secured to a proximal end of the insertion portion 2.

The insertion portion 2 includes: a tubular sheath 4; an operating wire 5 that is disposed inside the sheath 4 so as to be movable along a longitudinal-axis direction of the sheath 4; a basket wire (gripping portion) 6 that is provided at a distal end of the operating wire 5; a distal-end tip 7 that is secured to a distal end of the sheath 4; and a tube (resin member) 8 that is disposed in the sheath 4 and a distal end of which is secured to an outer surface of the distal-end tip 7.

The sheath 4 is, for example, a coil sheath that possesses flexibility that enables bending thereof in conformity to an insertion pathway and that possesses a high compressive strength.

The distal-end tip 7 is a metal cylindrical member and is secured to the distal end of the sheath 4 by means of a cylindrical connecting member in a coaxial manner.

The operating wire 5 is disposed over the entire length of the sheath 4 and is pulled toward a proximal end by the operating portion 3 on the proximal-end side of the sheath 4.

Figure 2:
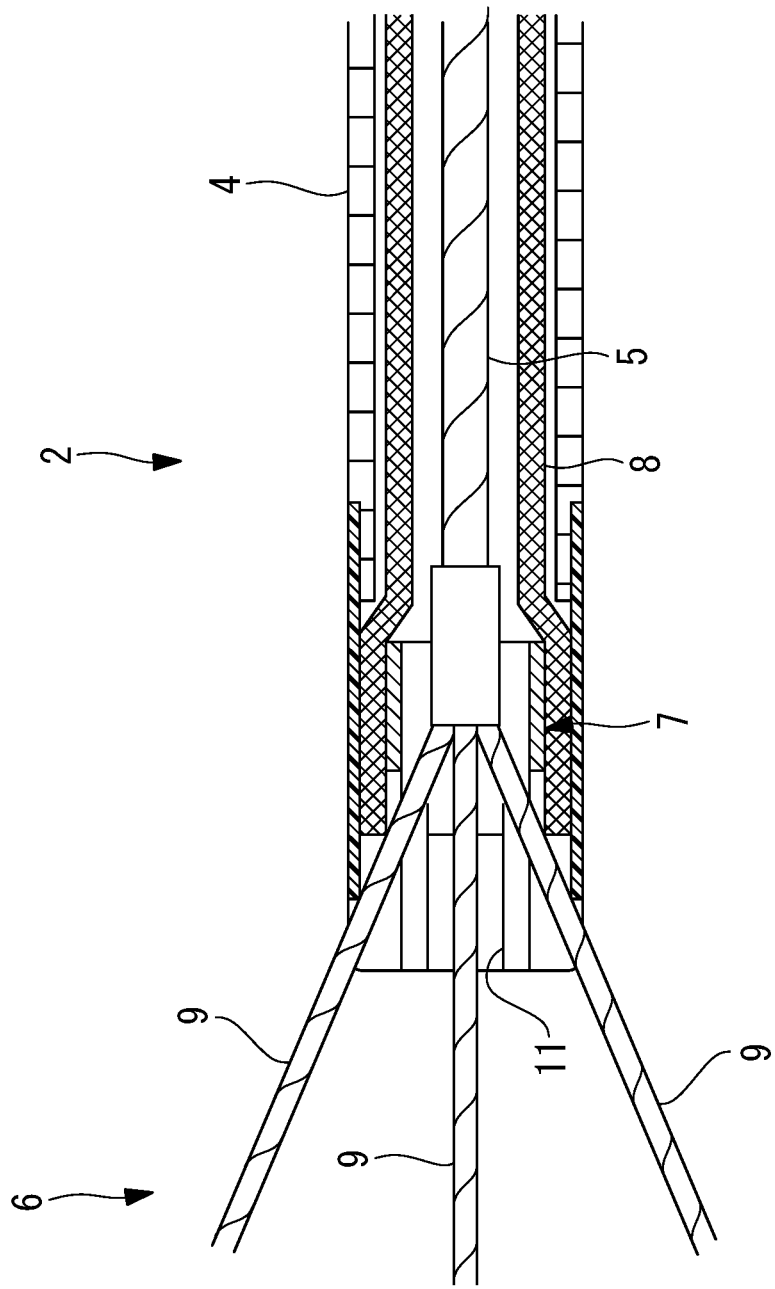
FIG. 2 is a partial longitudinal sectional view of a distal end of an insertion portion of the endoscope treatment tool in FIG. 1.

The basket wire 6: includes, for example, as shown in FIGS. 1 and 2, four wires 9 (only three of which are shown in the figure) in which proximal-end portions thereof are bundled at the distal end of the operating wire 5 and a distal-end member 10 that bundles distal-end portions of the wires 9 together; and forms a basket that can be accommodated in the sheath 4 as a result of the individual wires 9 being folded and that surrounds a prescribed space by being expanded, as shown in FIG. 1, as a result of being pushed out in the forward direction from the interior of the sheath 4.

Figure 3:
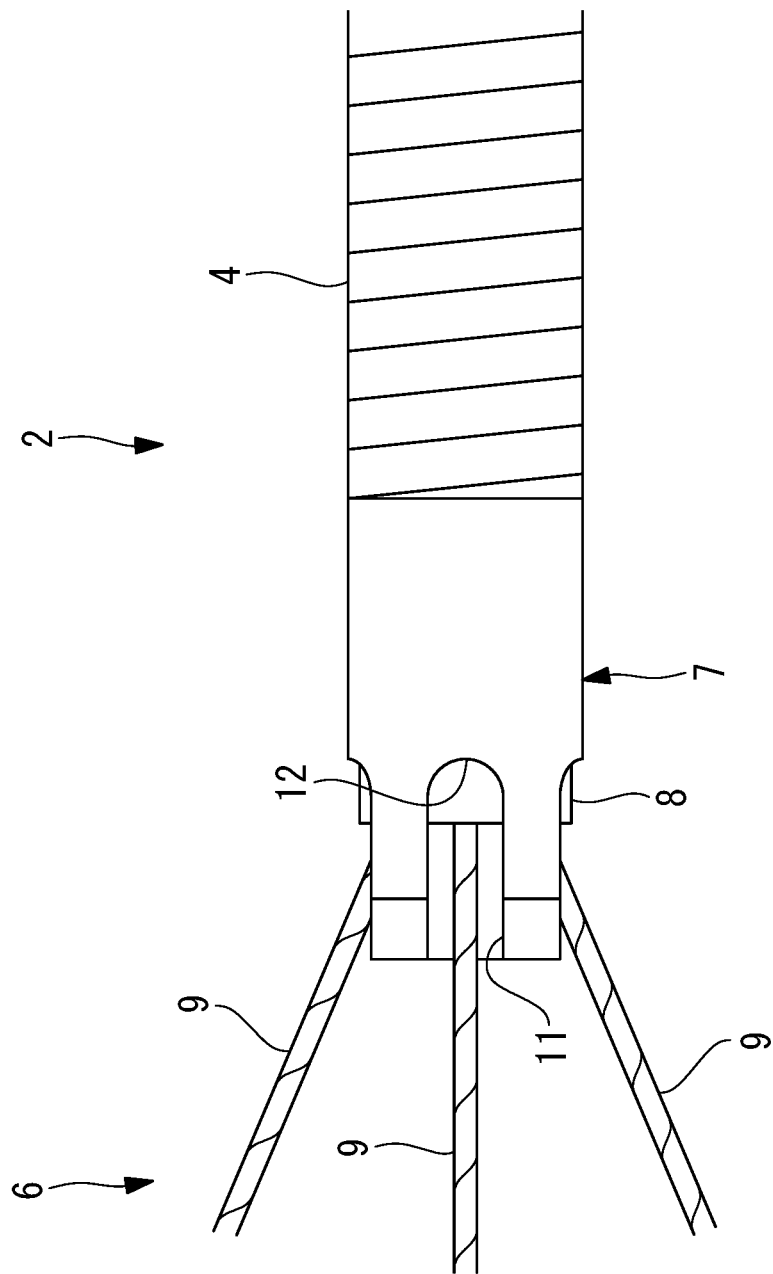
FIG. 3 is a partial side view of the distal end of the insertion portion of the endoscope treatment tool in FIG. 1.

The distal-end tip 7 is provided with a plurality of clearance grooves 11 that extend toward the proximal end from the distal end, as shown in FIGS. 2 and 3. Each of the clearance grooves 11 extends to a prescribed position in the longitudinal-axis direction parallel to the longitudinal axis of the distal-end tip 7. In the example shown in FIGS. 2 and 3, the clearance grooves 11 are provided at four locations with spacings therebetween in a circumferential direction in order to respectively accommodate the four wires 9 constituting the basket wire 6.

Each of the clearance grooves 11 has a groove width that is greater than the diameter of each of the wires 9 constituting the basket wire 6.

The tube 8 is formed of a resin having high slipperiness, such as a PEEK or a fluororesin (for example, a tetrafluoroethylene resin).

The tube 8 is disposed between the operating wire 5 and the sheath 4 as a result of being disposed inside the sheath 4, serves as a lining of an inner surface of the sheath 4, and reduces the friction generated between the operating wire 5 and the sheath 4.

In this embodiment, the tube 8 is disposed at a position at which an outer circumferential surface of the distal-end tip 7 is partially covered on the proximal-end side of the distal-end tip 7, as shown in FIG. 2. In other words, the tube 8 covers the outer circumferential surface of the distal-end tip 7 up to a position at which a distal-end surface thereof is disposed at an intermediate position in the longitudinal-axis direction of the distal-end tip 7. As shown in FIGS. 2 and 3, the distal-end surface of the tube 8 is disposed farther on a distal-end side than proximal ends 12 of the clearance grooves 11 provided in the distal-end tip 7 are.

More specifically, at least the proximal-end sides of the clearance grooves 11 overlap with the tube 8 in a radial direction of the distal-end tip 7. Also, the distal-end surface of the tube 8 is positioned farther on the proximal-end side of the distal-end tip 7 than the distal end of the distal-end tip 7 is and farther on a distal-end side of the distal-end tip 7 than the proximal ends 12 of the clearance grooves 11 are.

Figure 4:
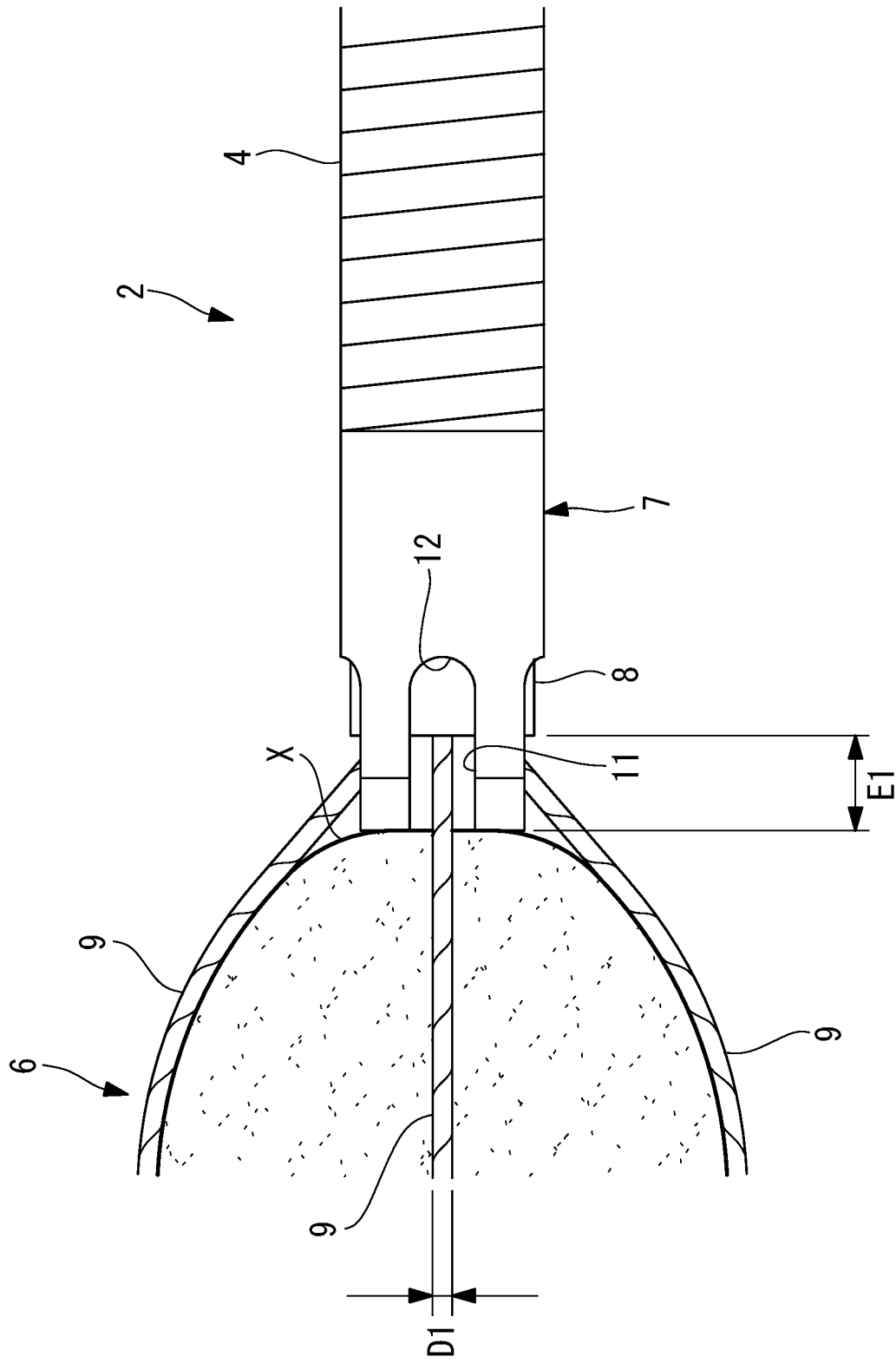
FIG. 4 is a partial side view of the insertion portion showing a state in which a calculus is gripped by the endoscope treatment tool in FIG. 1.
Figure 5:
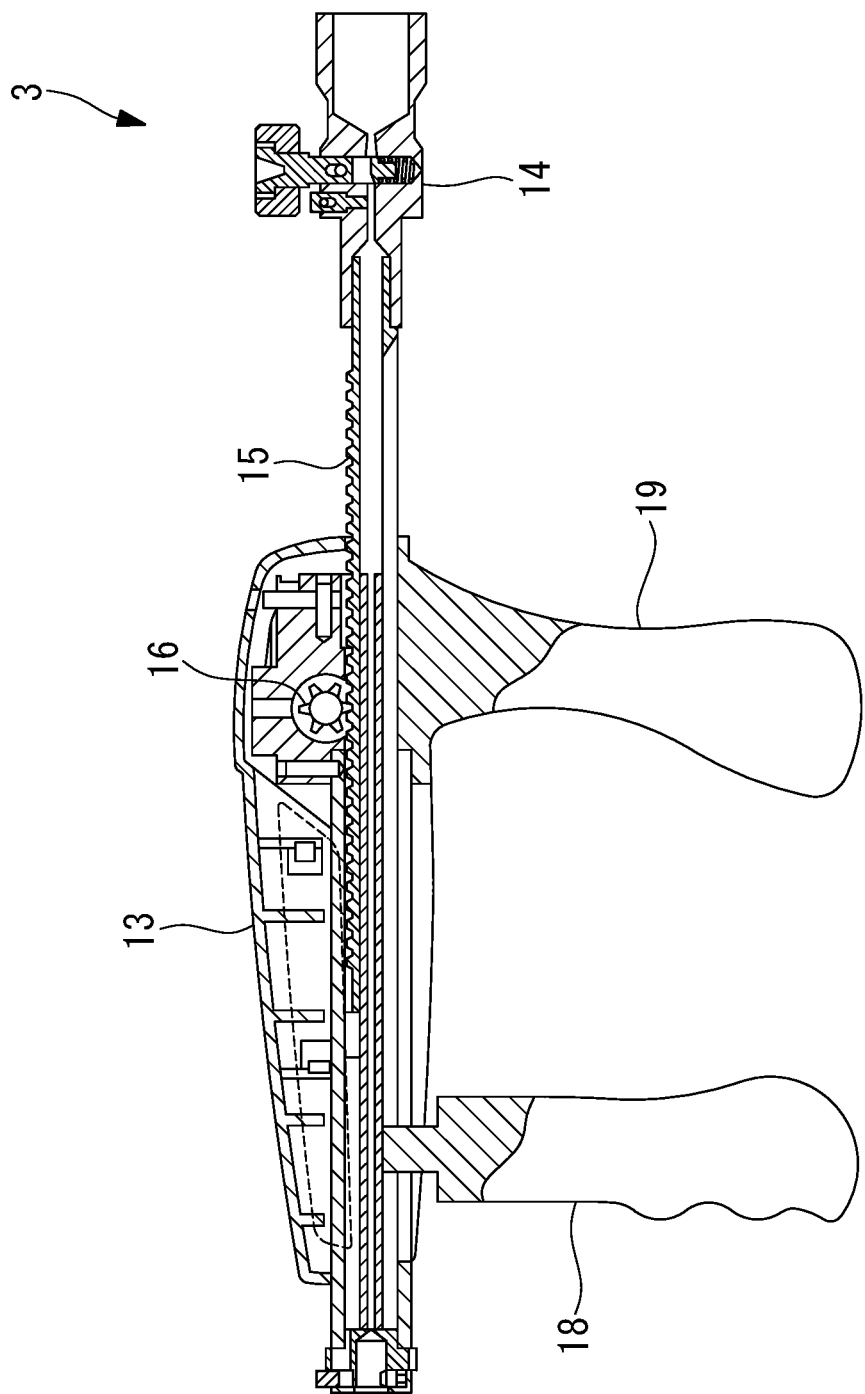
FIG. 5 is a longitudinal sectional view of an operating portion of the endoscope treatment tool in FIG. 1.
Figure 6:
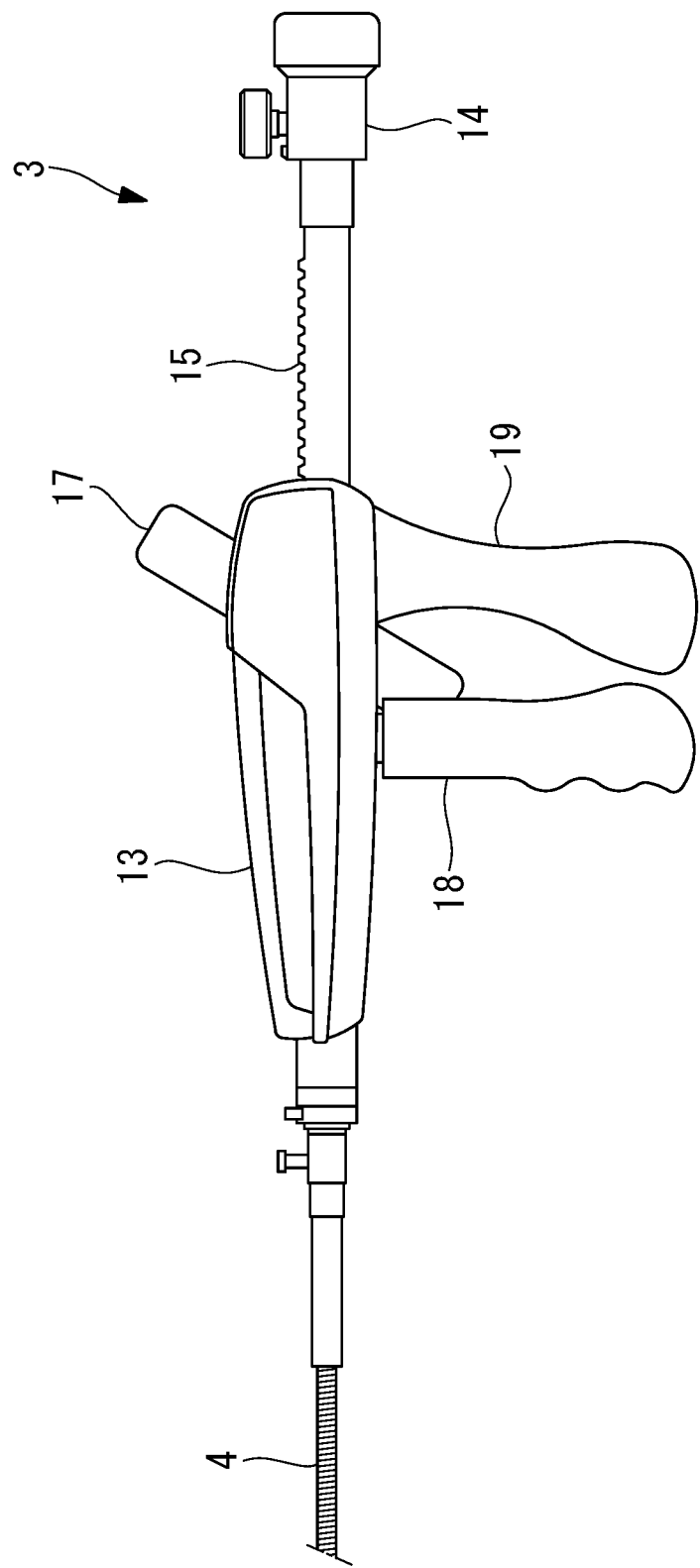
FIG. 6 is a side view of the operating portion in FIG. 5.

In this case, as shown in FIG. 4, it is desirable that a distance E1 between the distal end of the distal-end tip 7 and the distal-end surface of the tube 8 be greater than an outer diameter D1 of each of the wires 9 constituting the basket wire 6.

The operating portion 3 includes, for example, as shown in FIG. 1 and FIGS. 5 to 7: a body 13 connected to the proximal end of the sheath 4; a joining member 14 that is provided so as to be movable in a front-to-rear direction with respect to the body 13 and that is connected to the operating wire 5; a first handle 17 including a pinion gear 16 that engages with a rack gear 15 provided in the joining member 14; a second handle 18 that is secured to the joining member 14; and a support portion 19 that is secured farther on a proximal-end side of the body 13 than the second handle 18 is.

Figure 7:
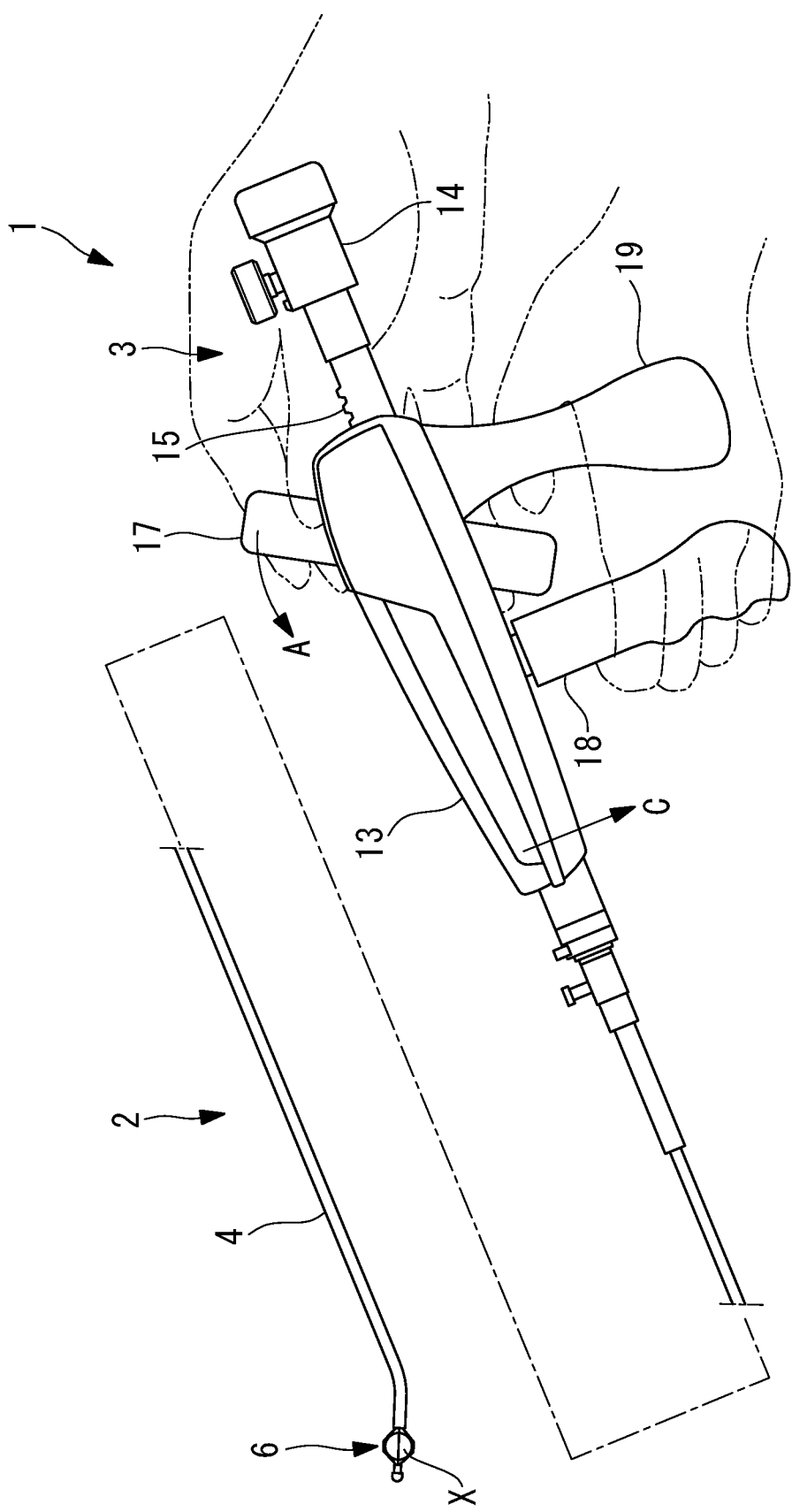
FIG. 7 is a side view showing a state in which the operating portion in FIG. 5 is being operated.
Figure 8:
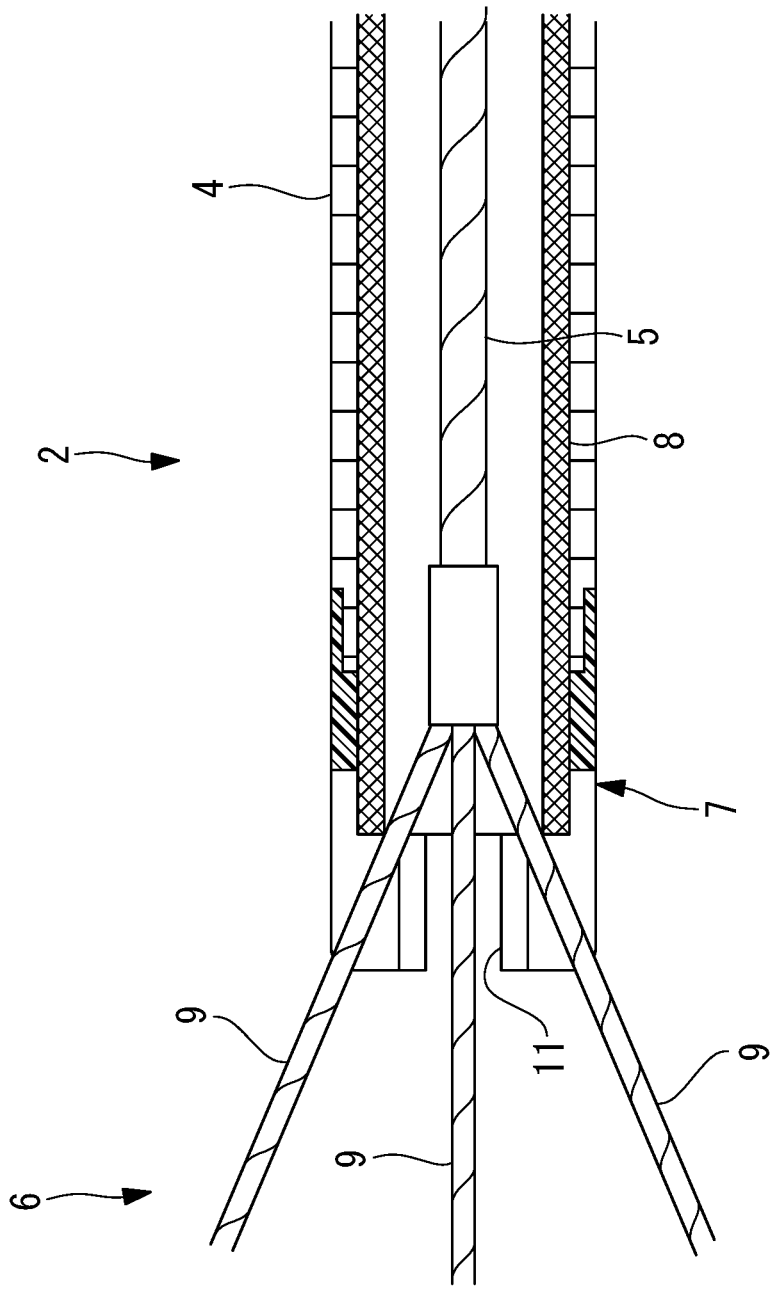
FIG. 8 is a partial longitudinal sectional view of a distal end of an insertion portion of an endoscope treatment tool according to a second embodiment of the present invention.

When operating the operating portion 3, as shown in FIG. 7, the thumb of the left hand is placed on the support portion 19, the index finger to the little finger of the left hand are placed on the second handle 18, and the second handle 18 is moved, by means of the gripping force of the left hand, in a direction in which the second handle 18 approaches the support portion 19. Accordingly, the joining member 14 to which the second handle 18 is secured is moved toward the proximal end with respect to the body 13, and the operating wire 5 secured to the joining member 14 is pulled toward the proximal end.

In addition, as a result of rotating the first handle 17 with respect to the body 13 by means of the right hand, the pinion gear 16 secured to the first handle 17 is rotated, and the rack gear 15 with which the pinion gear 16 is engaged is moved toward the proximal end of the body 13. Accordingly, the joining member 14 to which the rack gear 15 is secured is moved toward the proximal end of the body 13, and the operating wire 5 secured to the joining member 14 is pulled toward the proximal end.

The operation of the thus-configured endoscope treatment tool 1 according to this embodiment will be described below.

In order to crush a calculus X in the body of a patient by employing the endoscope treatment tool 1 according to this embodiment, the basket wire 6 is set to the contracted state by retracting the basket wire 6 into the sheath 4 by operating the operating portion 3 disposed at the proximal end of the sheath 4, the insertion portion 2 is inserted into a channel of an endoscope (not shown) inserted into a body cavity, and the distal end of the distal-end tip 7 of the endoscope treatment tool 1 is disposed in a state in which said distal end is in the close proximity of the calculus X in the body.

In this state, a surgeon operates the operating portion 3, which is disposed outside the body of the patient, the operating wire 5 is consequently pushed out toward the distal end, and thus, the basket wire 6 is made to protrude forward from the distal end of the distal-end tip 7. As a result of being pushed out in the forward direction from the distal-end tip 7, the basket wire 6 is deployed by being released from the contracted state. In this state, the calculus X is captured into the interior of the basket wire 6, and the operating wire 5 is pulled toward the proximal end as a result of the operating portion 3 being operated.

When the operating wire 5 is pulled toward the proximal end, the individual wires 9 constituting the basket wire 6 are retracted into the distal-end tip 7. Then, after the calculus X gripped by the basket wire 6 is pulled until reaching a position at which the calculus X abuts against the distal-end tip 7, an additional pulling force is applied to the operating wire 5. By doing so, the calculus X, which is trapped between the basket wire 6 and the distal end of the distal-end tip 7, is crushed.

In this case, because the clearance grooves 11 are provided in the distal-end tip 7 and the individual wires 9 are accommodated in the clearance grooves 11, the individual wires 9 constituting the basket wire 6 are prevented from being caught between the calculus X and the distal-end tip 7 even if the operating wire 5 is pulled until the calculus X abuts against the distal end of the distal-end tip 7.

Also in this state, because the distal end of the tube 8 is disposed farther on the distal-end side than the proximal ends 12 of the clearance grooves 11 are, the respective wires 9 accommodated in the clearance grooves 11 come into contact with the distal end of the tube 8, and thus, the respective wires 9 are prevented from coming into contact with the proximal ends 12 of the clearance grooves 11. In other words, the wires 9 in a state in which high tensile forces are acting thereon due to the pulling are prevented from being pressed against the metal distal-end tip 7. Accordingly, because the wires 9 do not come into contact with the hard distal-end tip 7, the wires 9 are not strongly rubbed against the distal-end tip 7, and thus, it is possible to suppress deformation of the wires 9.

In the case in which the wires 9 cause the distal end of the tube 8 to be pressed down also, because the tube 8 is held by the inner circumferential surface of the distal-end tip 7 and deformation whereby the tube 8 gets into the clearance grooves 11 is not likely to occur, it is possible to keep the frictional forces generated between the wires 9 and the tube 8 low.

In addition, because the tube 8 against which the wires 9 are pressed is made of a resin, it is possible to keep the frictional forces generated between the wires 9 and the tube 8 low. Accordingly, it is possible to efficiently transmit the pulling force applied to the operating wire 5 to the basket wire 6 by reducing the loss due to friction, and there is an advantage in that it is possible to crush the calculus X gripped by the basket wire 6 with a lower pulling force.

In addition, with the operating portion 3, for example, the support portion 19 and the second handle 18 are gripped with the left hand, the second handle 18 is pulled toward the support portion 19 by means of the gripping force of the left hand, the first handle 17 is also rotated by the right hand, and thus, the operation whereby the joining member 14 is pulled toward the proximal end is performed by using both hands; therefore, it is possible to pull the operating wire 5 with a greater force, and thus, it is possible to more easily crush the calculus X.

In addition, in the case in which the first handle 17 is rotated in the direction of the arrow A, a moment that causes the body to be tilted in the direction of the arrow C acts when the tensile force increases, which makes it difficult to rotate the first handle 17. With the operating portion 3 of this embodiment, because the second handle 18 is disposed farther on the front side than the rotation center of the first handle 17 is, it is possible to apply, to the body 13, a moment in the opposite direction of the arrow C by using the left hand gripping the second handle 18. Accordingly, it is possible to prevent the body 13 from tilting in the rotation direction of the first handle 17, and thus, there is an advantage in that a force is easily applied to the first handle 17.

Next, an endoscope treatment tool according to a second embodiment of the present invention will be described below with reference to the drawings.

In describing this embodiment, the same reference signs will be assigned to portions having the same configurations as the endoscope treatment tool 1 according to the first embodiment, described above, and the descriptions thereof will be omitted.

As shown in FIGS. 8 to 11, the endoscope treatment tool according to this embodiment and that of the first embodiment differ from each other in that the tube 8 and the sheath 4 are not secured to each other in this embodiment. The tube 8 is disposed on an inner-surface side of the distal-end tip 7 so as to be movable in the longitudinal-axis direction.

The length of the sheath 4 is composed of a coil sheath along the center axis of the sheath 4 increases as a result of being bent, because gaps among wire rods constituting the coil sheath widen.

Figure 10:
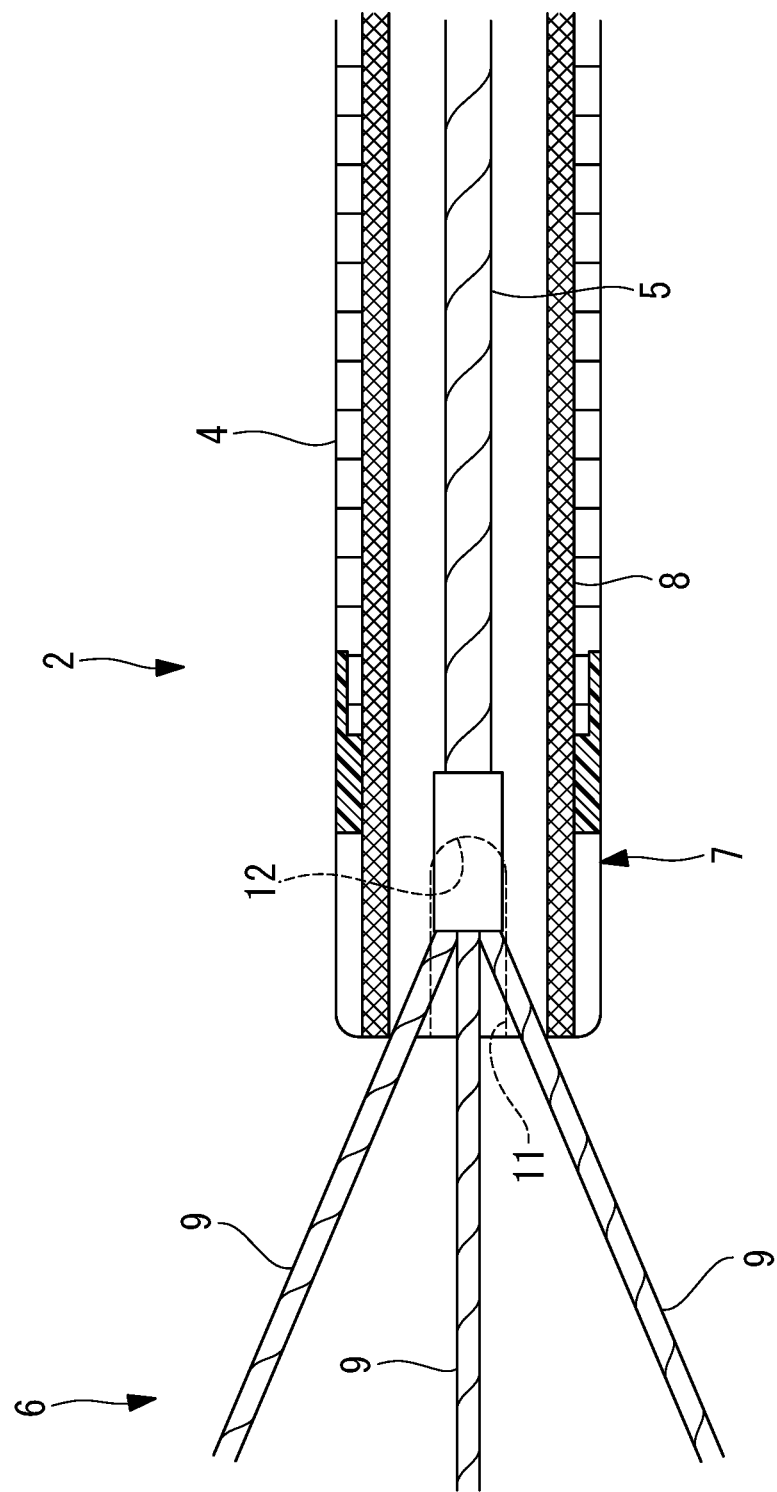
FIG. 10 is a partial longitudinal sectional view of the insertion portion showing a case in which the position of the tube with respect to the sheath is moved closer toward a distal end as compared with FIG. 8.
Figure 11:
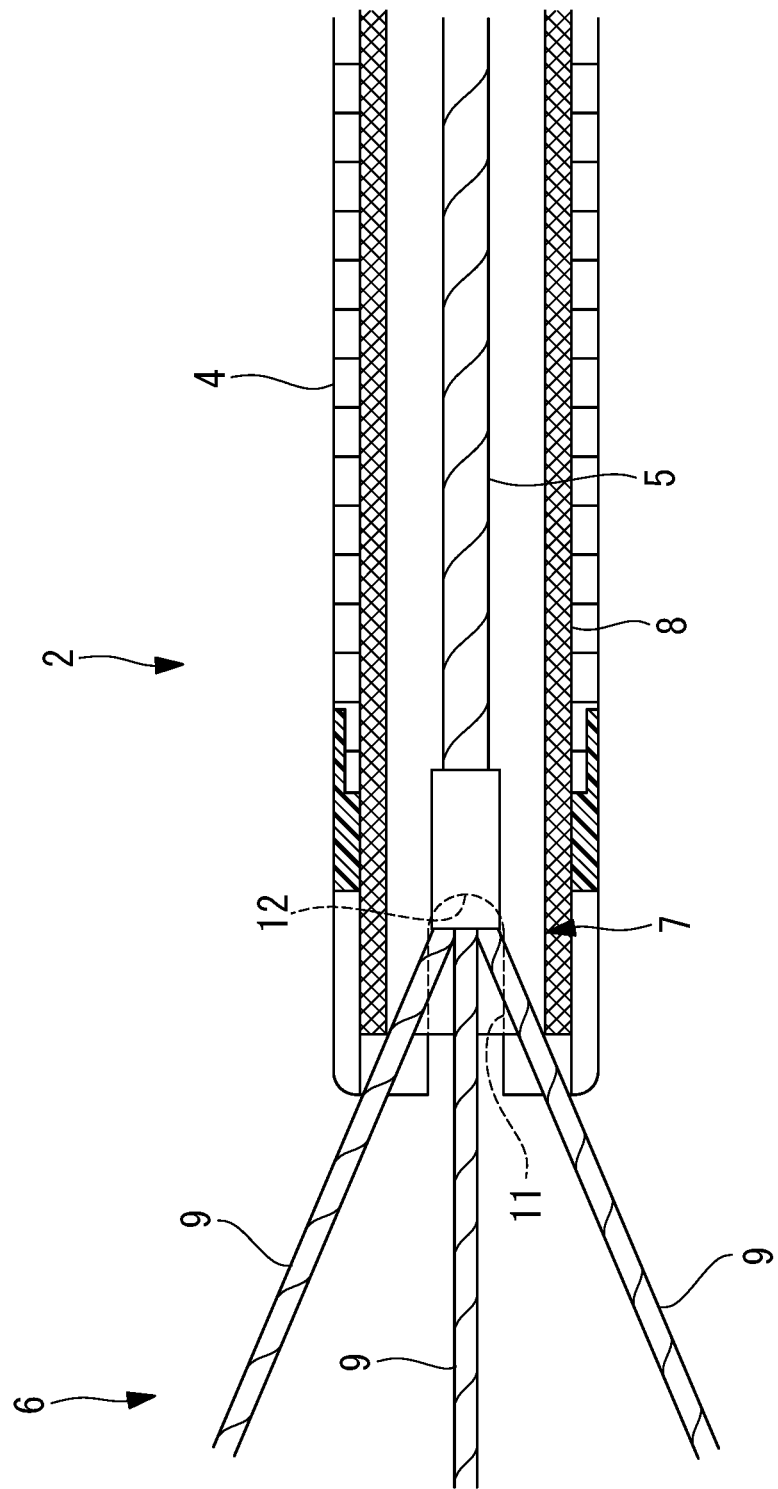
FIG. 11 is a partial longitudinal sectional view of the insertion portion showing a state in which the position of the tube is moved closer toward the proximal end as compared with FIG. 10 as a result of the sheath being extended.

For example, even if the distal end of the tube 8 is aligned with the distal end of the distal-end tip 7 in a straight state, as shown in FIG. 10, the tube 8 moves inside the sheath 4 when the sheath 4 bends, and the distal end of the tube 8 moves farther toward the proximal end than the distal end of the distal-end tip 7, as shown in FIG. 11.

In this embodiment, in the assumed use state, the tube 8 and the sheath 4 are in a positional relationship in which the tube 8 is caught between the wires 9 and the proximal ends 12 of the clearance grooves 11 of the sheath 4 even in the state in which the distal end of the tube 8 has moved maximally toward the proximal end with respect to the sheath 4.

Figure 9:
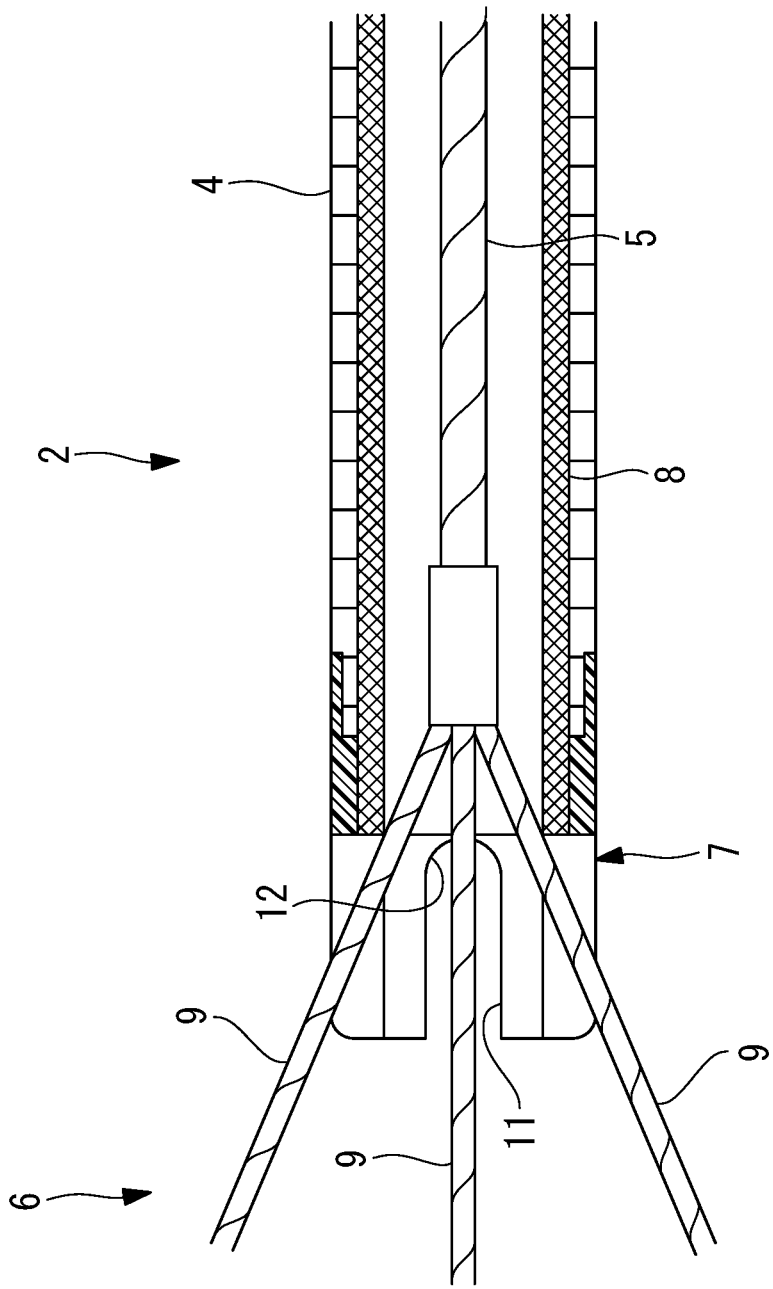
FIG. 9 is a partial longitudinal sectional view of the insertion portion showing a case in which the position of a tube with respect to a sheath is moved closer toward a proximal end as compared with FIG. 8.

The state in which the distal end of the tube 8 has moved maximally toward the proximal end is, for example, a state in which the distal end of the tube 8 is positioned so as to be aligned with side surfaces of the clearance grooves 11 on the proximal-end side, as shown in FIG. 9.

The operation of the thus-configured endoscope treatment tool according to this embodiment will be described below.

With the endoscope treatment tool according to this embodiment also, when a tensile force acts on the wires 9 as a result of the operating wire 5 being pulled, the calculus X captured into the basket wire 6 is retracted to the position at which the calculus X abuts against the distal end of the distal-end tip 7. In this case also, because the respective wires 9 constituting the basket wire 6 are accommodated in the clearance grooves 11 of the distal-end tip 7, the individual wires 9 are prevented from being caught between the distal-end tip 7 and the calculus X.

In addition, in this embodiment also, because the tube 8 is disposed between the wires 9 and the distal-end tip 7, the wires 9 are prevented from being directly pressed against the side walls of the clearance grooves 11 on the proximal-end side, even if large tensile forces act on the respective wires 9 constituting the basket wire 6. In other words, because the wires 9 come into contact with the resin tube 8 having greater slipperiness than the metal distal-end tip 7, it is possible to efficiently transmit the pulling force to the basket wire 6 by reducing the loss due to friction, and it is possible to crush the calculus X gripped by the basket wire 6 with a lower pulling force.

With the endoscope treatment tool according to this embodiment, because the tube 8 is disposed on the inner-surface side of the distal-end tip 7, there is an advantage in that it is possible to more reliably position the tube 8 between the wires 9 and the distal-end tip 7. In other words, the tube 8 deforms radially outward when large tensile forces act on the wires 9 and the wires 9 are pressed against the tube 8; however, because the distal-end tip 7 is disposed radially outside the tube 8, it is possible to more reliably prevent the wires 9 and the distal-end tip 7 from coming into contact with each other even if the tube 8 deforms.

Note that, in this embodiment, the positional relationship between the tube 8 and the sheath 4 is assumed to be a positional relationship in which the tube 8 is caught between the wires 9 and the proximal ends 12 of the clearance grooves 11 of the sheath 4 in the assumed use state, even in the state in which the distal end of the tube 8 is moved maximally toward the proximal end with respect to the sheath 4. In other words, although the proximal-end-side position of the distal end of the tube 8 is limited, the position thereof on the distal-end side may be arbitrary.

Figure 12:
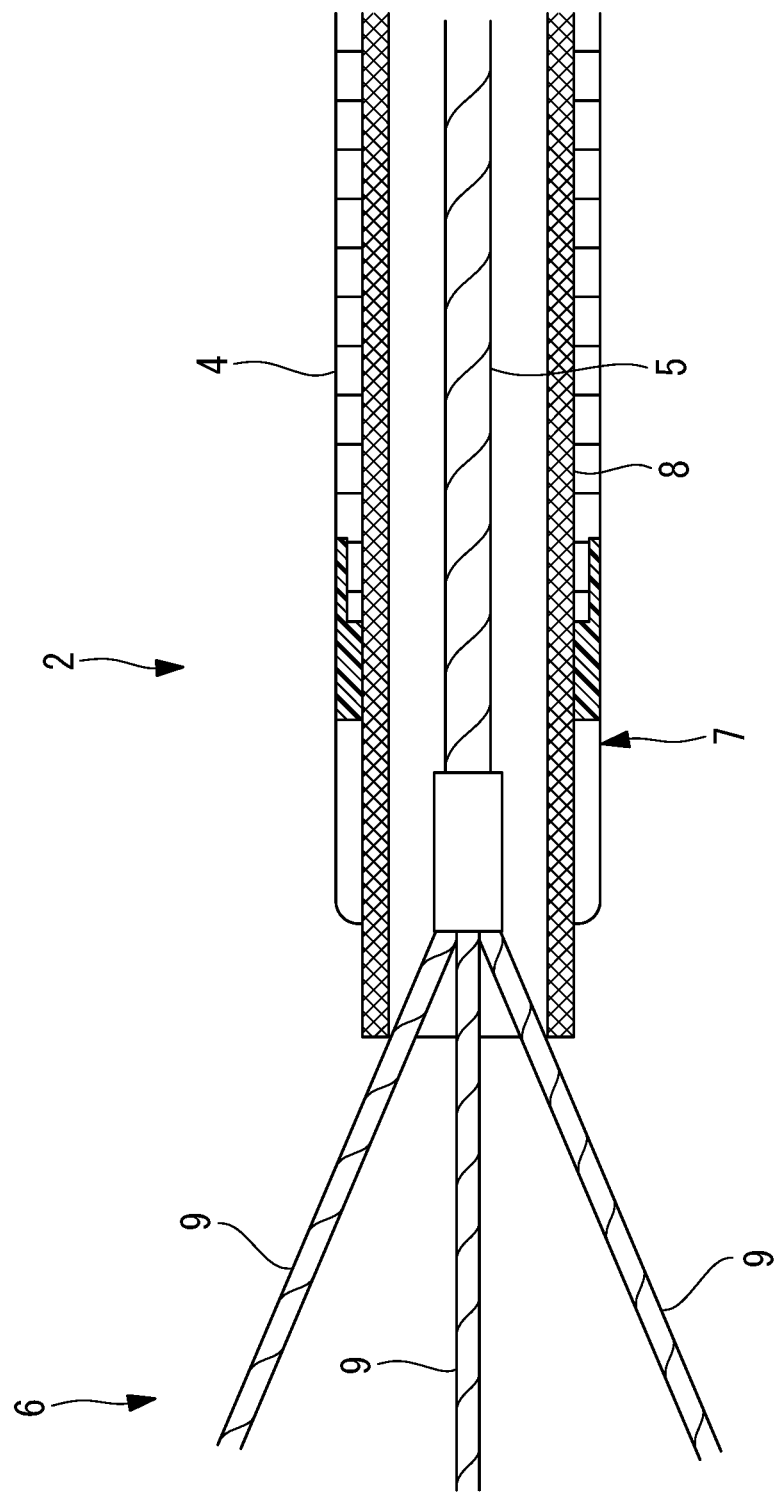
FIG. 12 is a partial longitudinal sectional view of the insertion portion showing a case in which the position of the tube with respect to the sheath is moved closer toward the distal end as compared with FIG. 10.

For example, the distal-end-side position of the tube 8 may be the same as the position of the distal end of the distal-end tip 7, as shown in FIG. 10, or the tube 8 may be disposed at a position at which the tube 8 protrudes from the distal end of the distal-end tip 7, as shown in FIG. 12.

Figure 13:
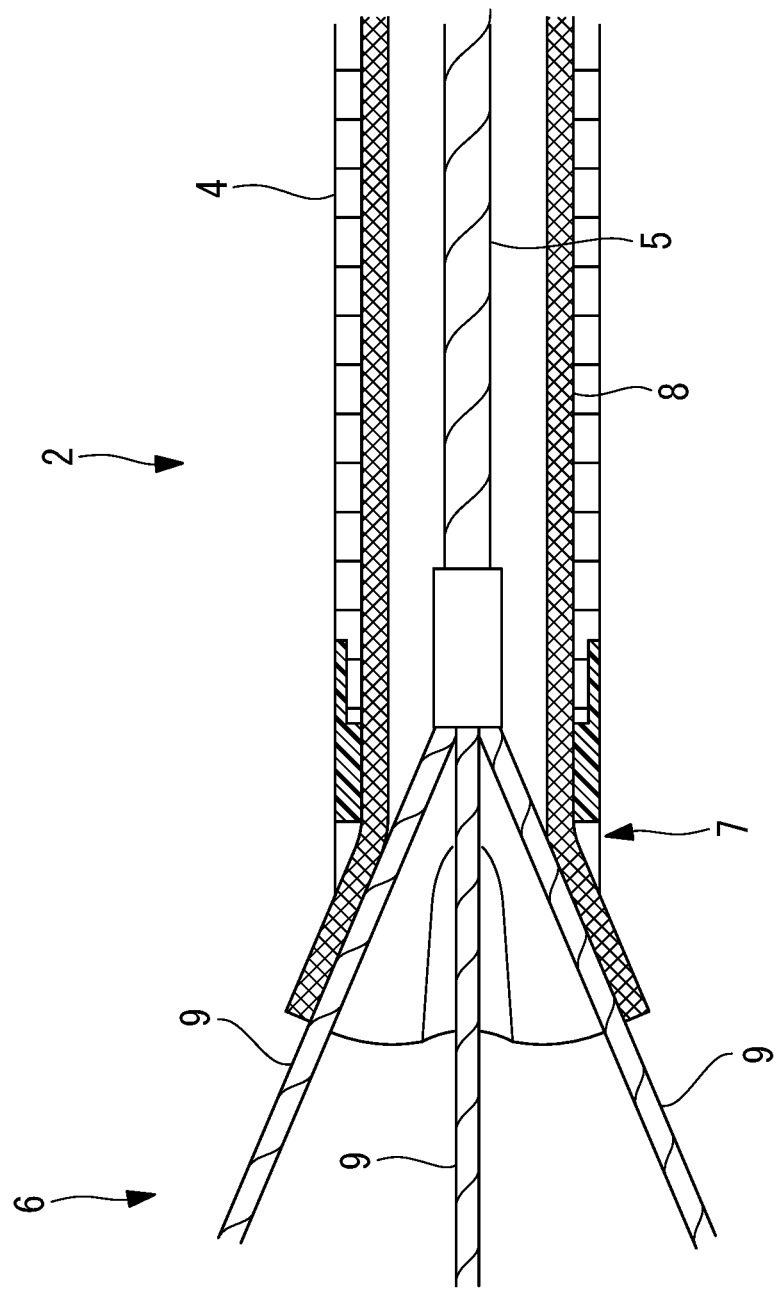
FIG. 13 is a partial longitudinal sectional view of the insertion portion for explaining deformation of the tube when a wire is pulled in the case of FIGS. 10 and 12.
Figure 14:
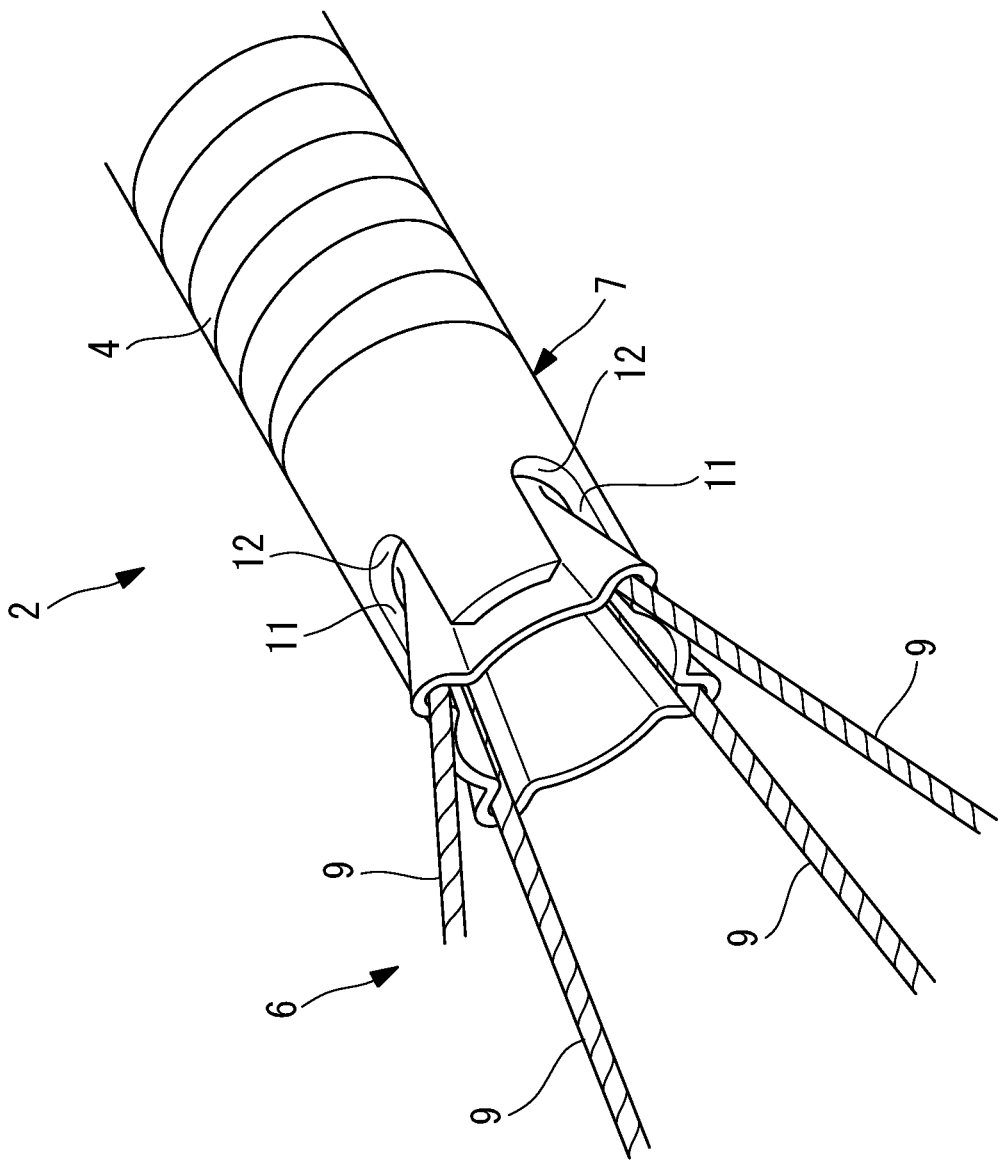
FIG. 14 is a partial perspective view of the insertion portion for explaining deformation of the tube in FIG. 13.

Even in the case in which large tensile forces act on the wires 9 in the states in FIGS. 10 and 12, because the tube 8 against which the wires 9 are pressed partially deforms so as to get into the clearance grooves 11 and the wires 9 are accommodated in the clearance grooves 11, as shown in FIGS. 13 and 14, the wires 9 are prevented from being caught between the calculus X and the distal-end tip 7, and the wires 9 are prevented from coming into direct contact with the clearance grooves 11.

Figure 15:
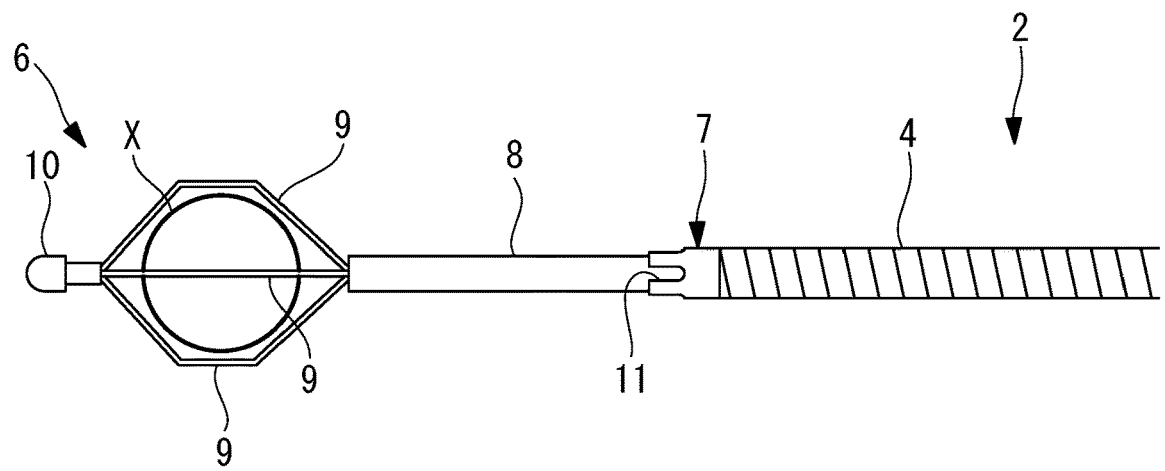
FIG. 15 is a partial side view of the insertion portion showing a case in which the position of the tube with respect to the sheath is moved even closer toward the distal end as compared with FIG. 10.
Figure 16:
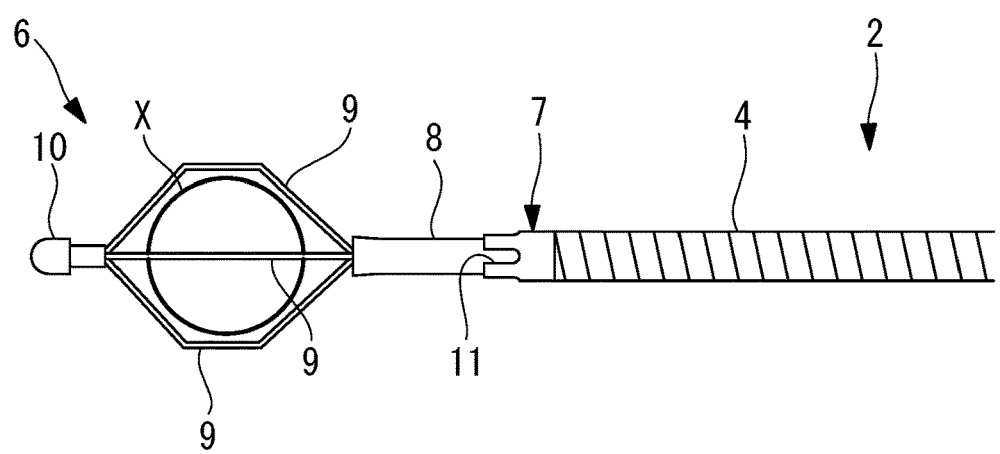
FIG. 16 is a partial side view of the insertion portion showing a state in which the tube is retracted into the sheath more as compared with FIG. 15.
Figure 17:
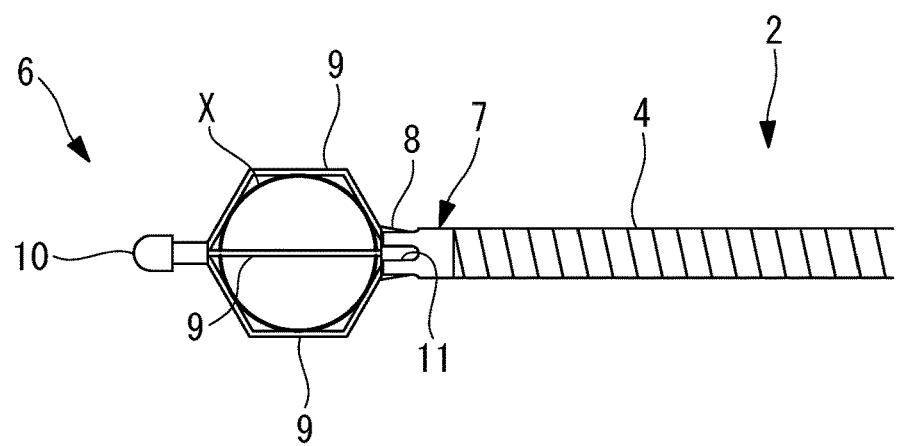
FIG. 17 is a partial side view of the insertion portion showing a state in which the tube is retracted into the sheath more as compared with FIG. 16.

In addition, as shown in FIGS. 15 to 17, the distal end of the tube 8 may protrude greatly beyond the distal end of the distal-end tip 7 in the state in which the calculus X is captured in the basket wire 6, because the tube 8 is retracted until the distal end of the tube 8 and the distal end of the distal-end tip 7 are substantially aligned with each other before crushing the calculus X when the operating wire 5 is pulled so long as the tube 8 is retracted into the sheath 4 by an amount that does not cause the tube 8 to buckle.

In addition, notches 20 having larger sizes than the outer diameters of the wires 9 may be provided at phases of the distal end of the tube 8 that are aligned with the clearance grooves 11 so that the wires 9 are accommodated in the clearance grooves 11 even if the tube 8 does not deform.

Figure 18:
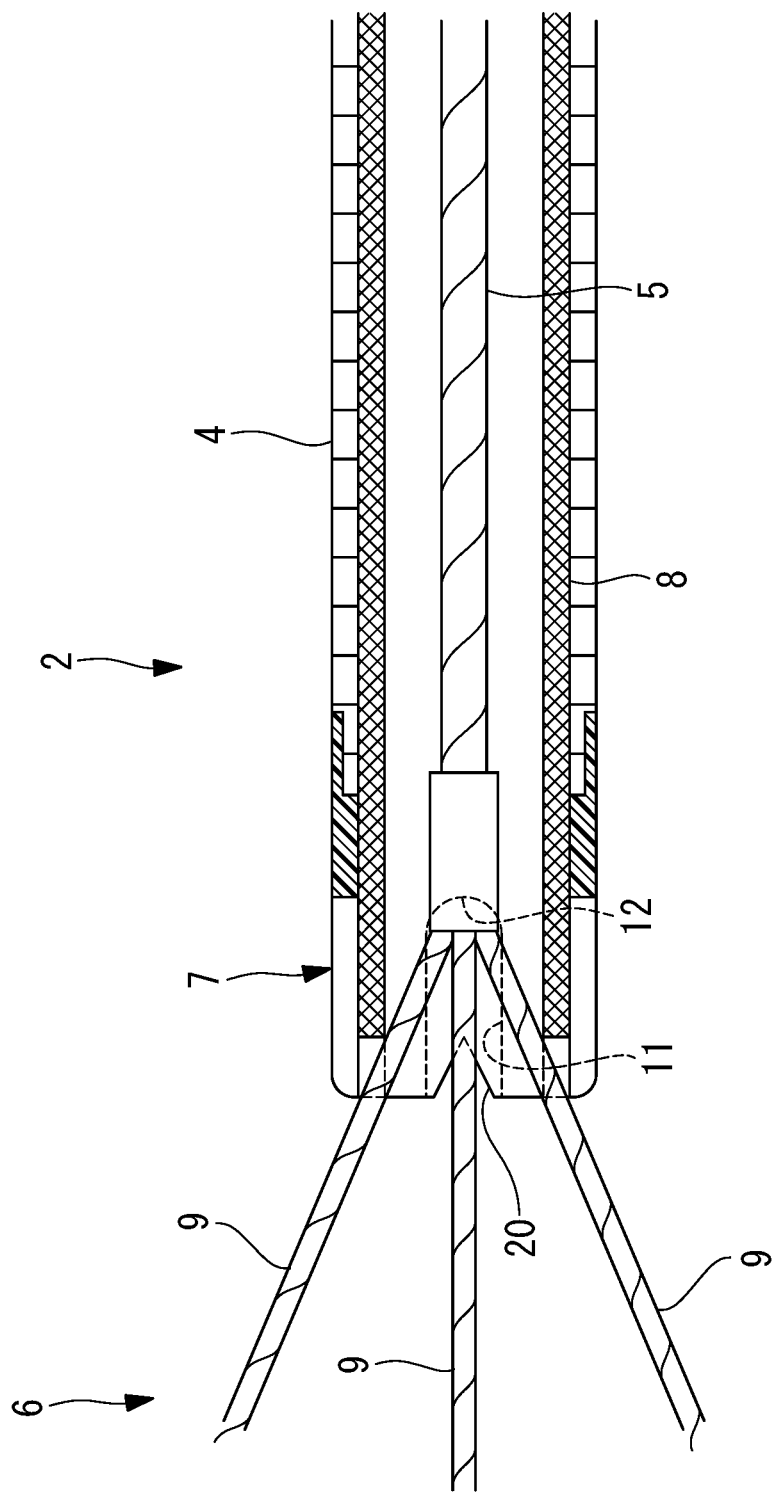
FIG. 18 is a partial longitudinal sectional view of the insertion portion in the case in which a distal end of the tube in FIG. 10 has a notch.
Figure 19:
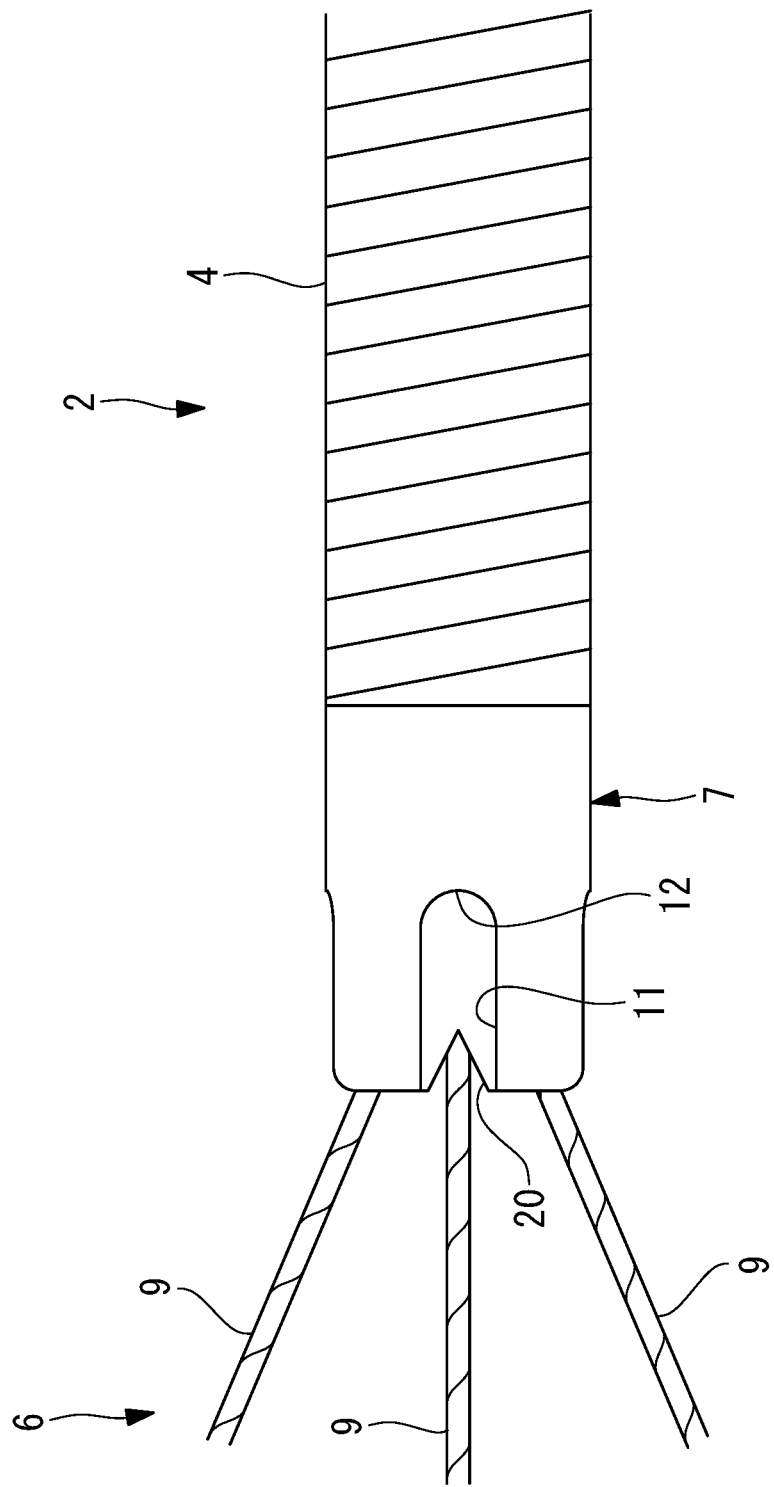
FIG. 19 is a partial side view of the insertion portion in FIG. 18.
Figure 20:
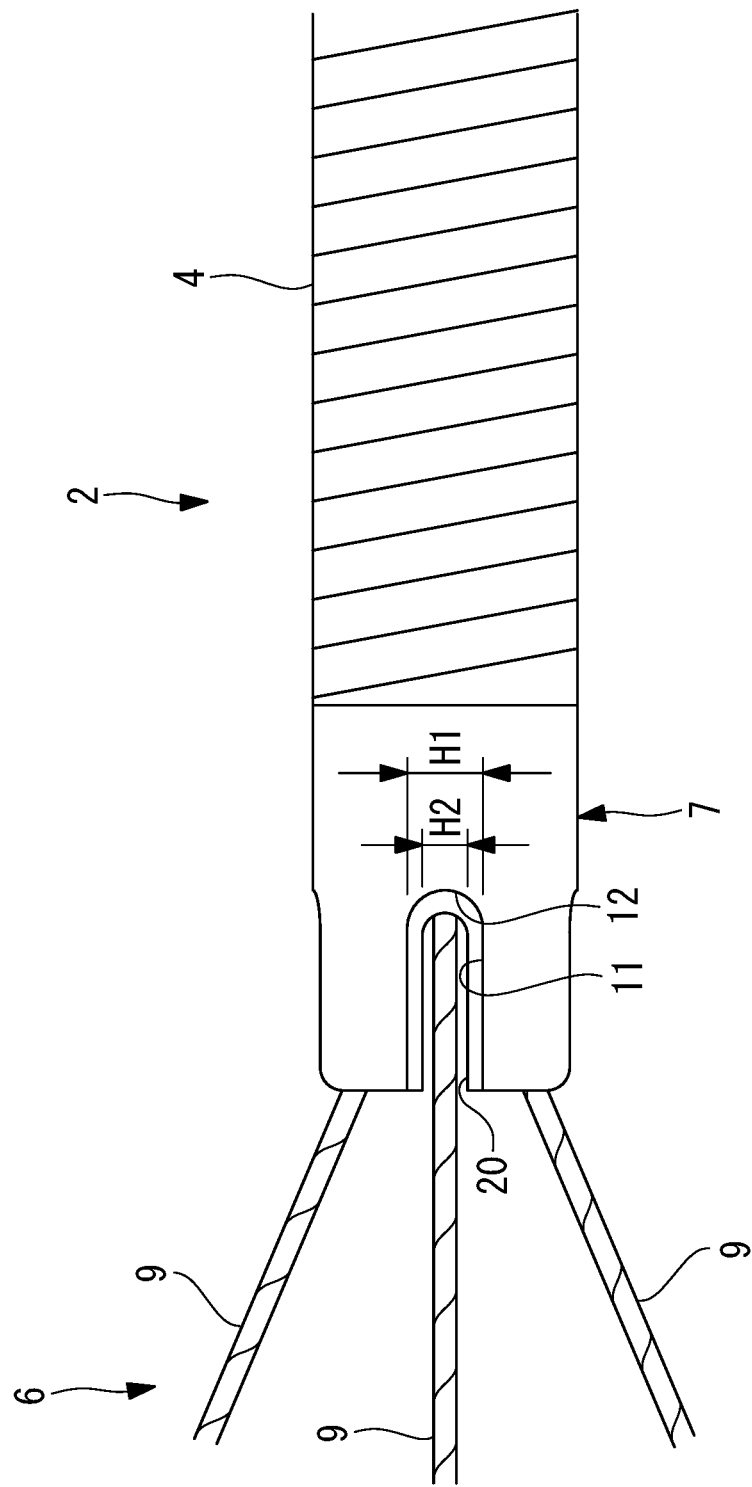
FIG. 20 is a partial side view of the insertion portion showing a modification of the notch in FIG. 18.

The shape of the notch 20 may be a V-shaped groove, as shown in FIGS. 18 and 19, or may be the same shape as that of the clearance groove 11, as shown in FIG. 20. In FIG. 20, assuming that the width of the clearance groove is H1 and that the width of the notch is H2, it is preferable that H1>H2 in order to eliminate contact between a wire 9 and the distal-end tip 7 as much as possible.

Figure 21:
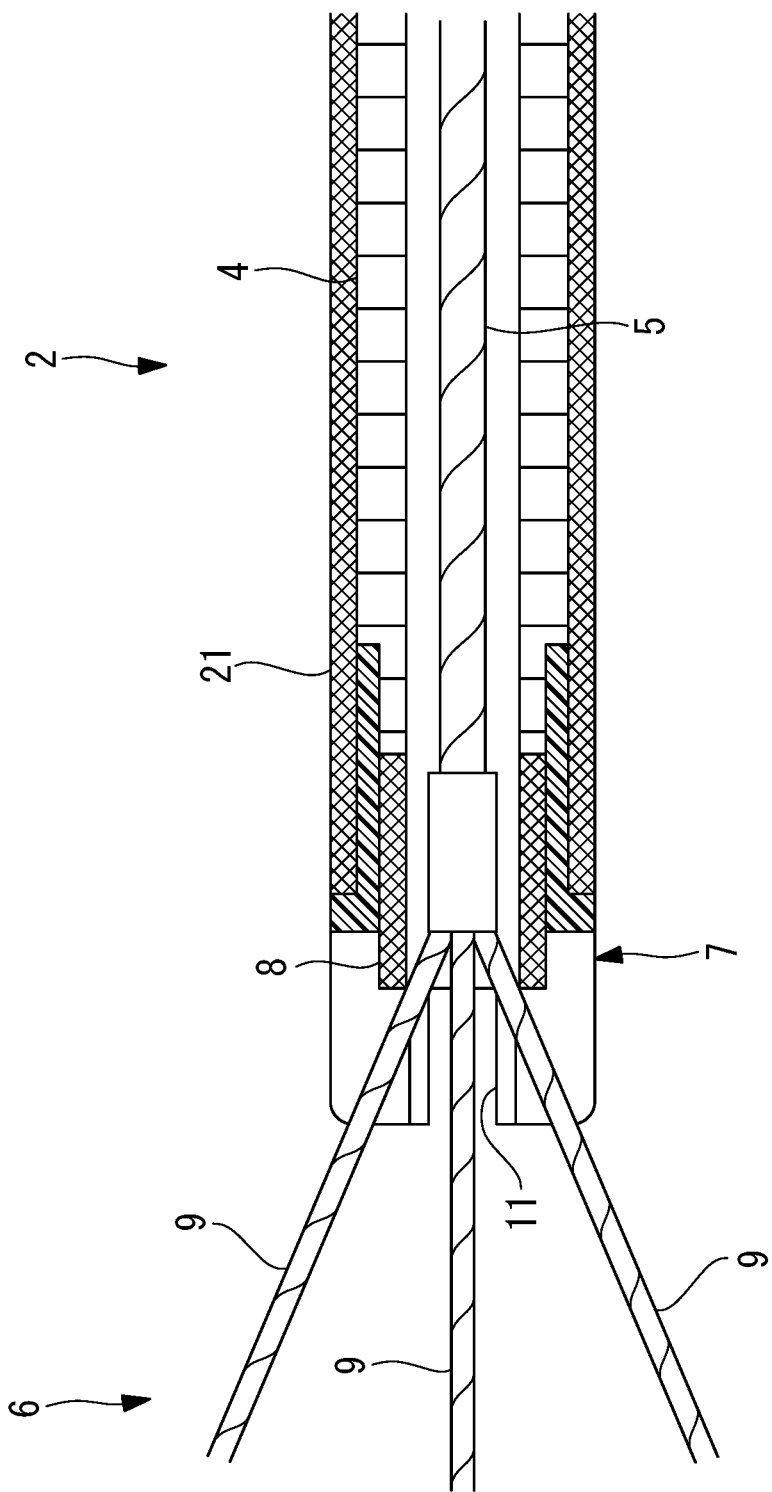
FIG. 21 is a partial longitudinal sectional view showing a modification of the insertion portion in FIG. 2.

In addition, this embodiment has been described by way of a case in which the tube 8 that is movable in the longitudinal direction with respect to the sheath 4 is disposed inside the sheath 4; however, alternatively, the distal-end tip 7 and a short tube 8 that is disposed at the inner surface of the distal-end tip 7 may be secured to the distal end of the sheath 4, as shown in FIG. 21. In this case also, it is preferable that the distal-end surface of the tube 8 be disposed farther on the distal-end side than the proximal ends 12 of the clearance grooves 11 of the distal-end tip 7 are. In the figure, reference sign 21 is a cover tube that covers an outer surface of the sheath 4. A distal end of the cover tube 21 is positioned farther on the proximal-end side of the distal-end tip 7 than the proximal ends 12 of the clearance grooves 11 are.

Figure 22:
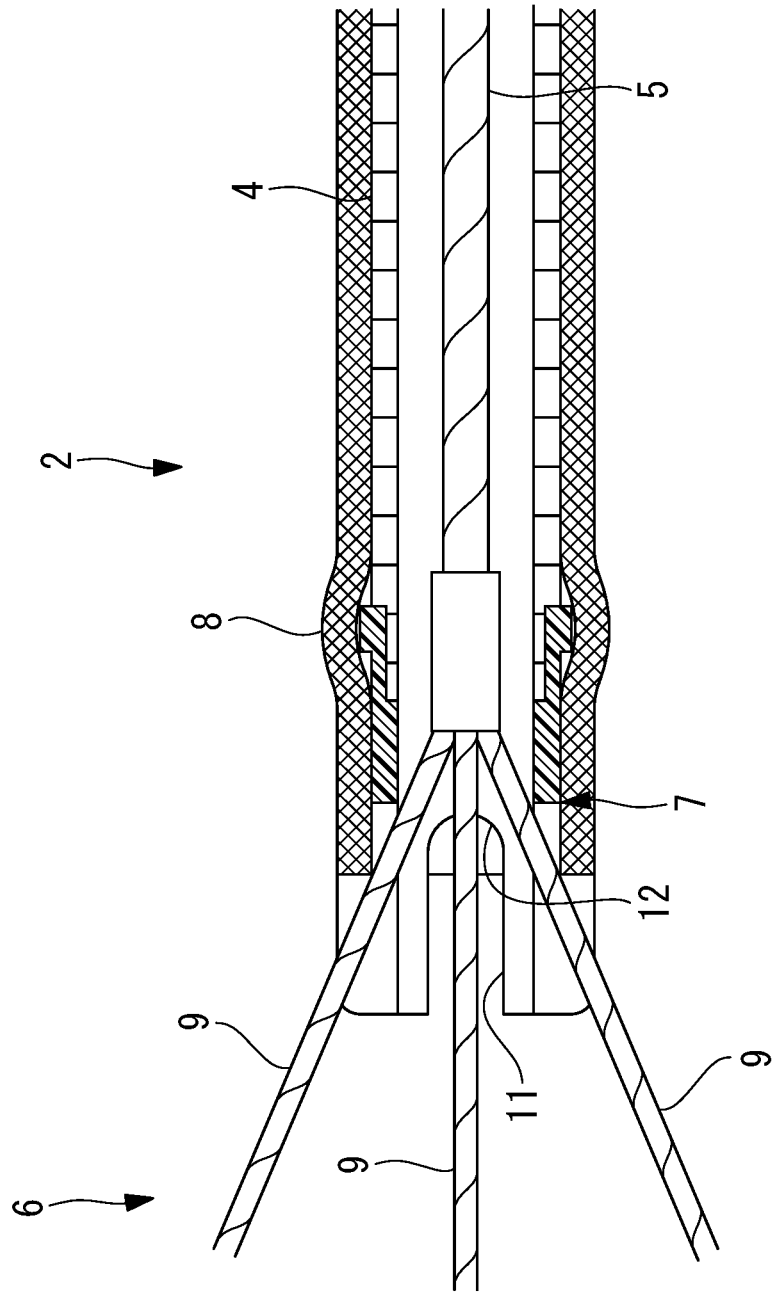
FIG. 22 is a partial longitudinal sectional view showing another modification of the insertion portion in FIG. 2.
Figure 23:
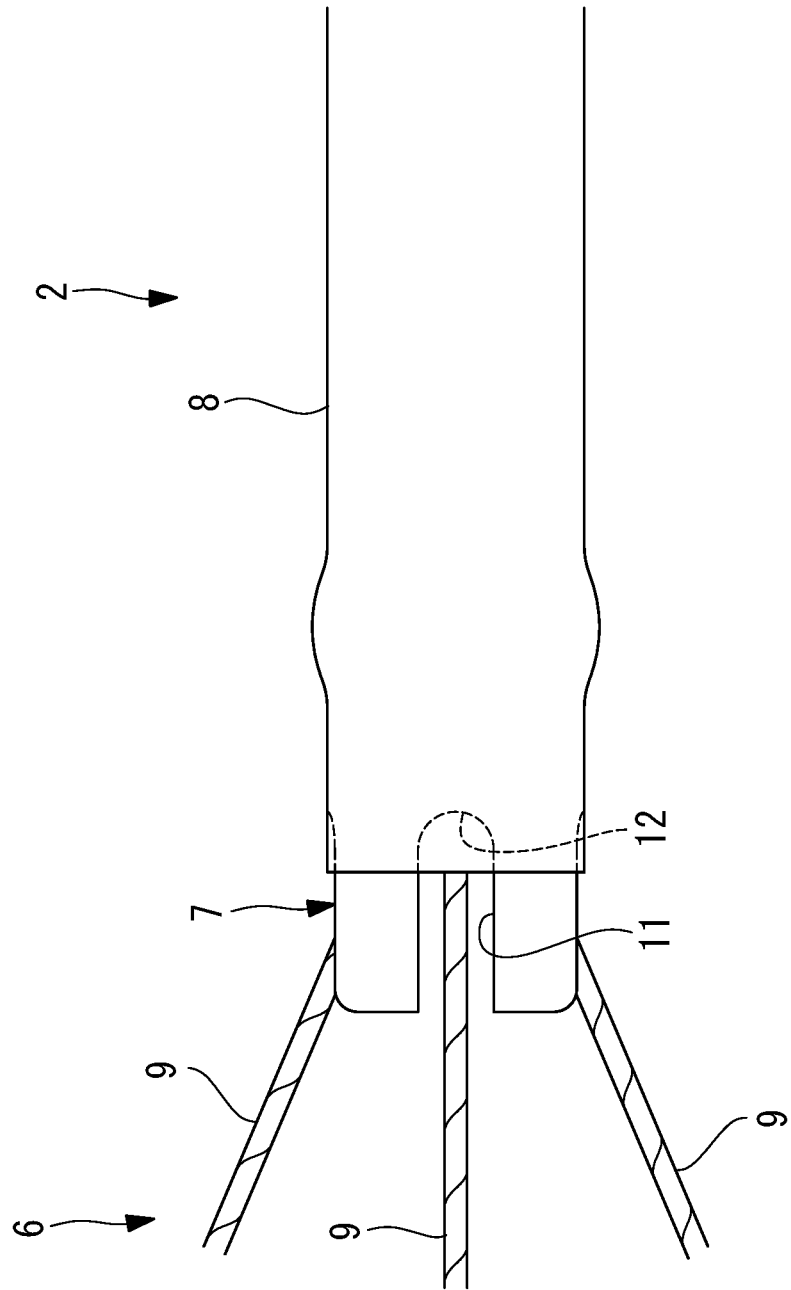
FIG. 23 is a side view of the insertion portion in FIG. 22.

In addition, the endoscope treatment tool 1 according to this embodiment has been described by way of an example in which the tube 8 is disposed inside the sheath 4; however, alternatively, the tube 8 may be disposed outside the sheath 4, as shown in FIGS. 22 and 23.

Specifically, the tube 8 covers the outer surface of the sheath 4 and a portion of the outer surface of the distal-end tip 7 in a section from the proximal end of the sheath 4 to intermediate positions of the clearance grooves 11 of the distal-end tip 7. In this case also, the distal-end surface of the tube 8 needs to be disposed farther on the distal-end side than the proximal ends 12 of the clearance grooves 11 of the distal-end tip 7 are.

Figure 24:
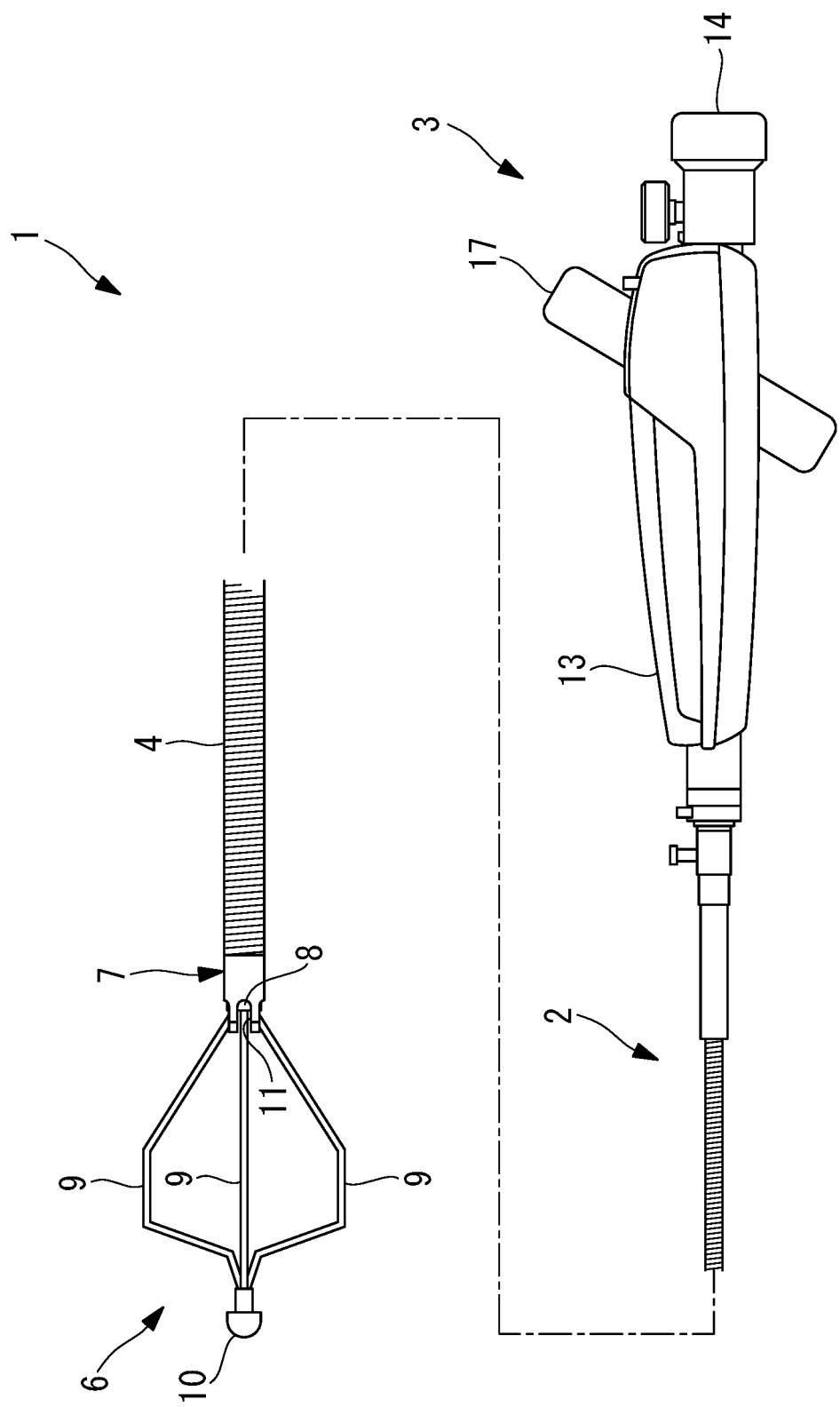
FIG. 24 is an overall configuration diagram showing a modification of the operating portion in FIG. 1.

In addition, a structure that includes the first handle 17 in the body 13 and that does not have the second handle 18 and the support portion 19, as shown in FIG. 24, may be employed as the operating portion 3.

In addition, this embodiment has been described by way of an example in which the basket wire 6 is employed as a gripping portion; however, alternatively, a snare 20 may be employed, as shown in FIG. 25.

The above-described embodiment also leads to the following aspects.

An aspect of the present invention is an endoscope treatment tool including: a tubular sheath having a longitudinal axis; an operating wire that is disposed in an interior of the sheath so as to be movable along the longitudinal axis; a gripping portion that is provided at a distal end of the operating wire and that has one or more wires for gripping a calculus; a cylindrical metal distal-end tip that is attached to a distal end of the sheath; and a resin member that is disposed at a position adjacent to the distal-end tip on a radially inner side or outer side thereof, wherein the distal-end tip is provided with clearance grooves that extend toward a proximal end of the distal-end tip from a distal end of the distal-end tip, that pass therethrough from an inner circumferential surface of the distal-end tip to an outer circumferential surface of the distal-end tip, and that have sizes enabling the wires of the gripping portion to pass therethrough, and at least proximal-end sides of the clearance grooves overlap with the resin member in a radial direction of the distal-end tip and a distal end of the resin member is disposed farther on a distal-end side than proximal ends of the clearance grooves are.

With this aspect, the calculus is pressed against the distal end of the distal-end tip when the operating wire is pulled toward the proximal end in the state in which the distal-end tip and the distal-end portion of the sheath are disposed in the body and the calculus is gripped by the wires constituting the gripping portion provided at the distal end of the operating wire by operating the operating wire on the proximal-end side of the sheath, which is disposed outside the body. Because the wires constituting the gripping portion get into the clearance grooves provided at the distal end of the distal-end tip, the wires are not caught between the gripped calculus and the distal-end tip, and the wires are inserted into the clearance grooves so as to be inclined in the form that spreads out toward the distal end from the interior of the distal-end tip.

In this case, because the clearance grooves extend toward the proximal end of the distal-end tip from the distal end of the distal-end tip, the wires come close to groove walls of the clearance grooves on the proximal-end sides thereof depending on the angles of the wires being inserted into the clearance grooves. In this case also, the resin member is disposed adjacent to the distal-end tip on the radially inner side or outer side thereof and at least the proximal-end sides of the clearance grooves overlap with the resin member in the radial direction of the distal-end tip. Because the distal end of the resin member is disposed farther on the distal-end side than the proximal ends of the clearance grooves are, the wires come into contact with the resin member and are prevented from coming into contact with the proximal ends of the clearance grooves provided in the metal distal-end tip. Accordingly, because the wires do not come into contact with the hard distal-end tip, the wires are not strongly rubbed against the distal-end tip, and thus, it is possible to prevent the wires from being deformed.

In other words, even in the state in which large tensile forces are imparted to the wires as a result of being pulled, the frictional forces that act on the wires are kept low due to the contact with the resin member. Accordingly, it is possible to efficiently transmit the pulling force applied to the operating wire to the wires constituting the gripping portion, and thus, it is possible to crush the calculus gripped by the gripping portion by means of a lower pulling force.

In the above-described aspect, the resin member may be disposed radially inside the distal-end tip.

With this configuration, the wires that are inclined in the form that spreads out toward the distal end from inside the distal-end tip are pressed radially outward on the inner-surface side of the resin member. As the result of the resin member being disposed at a position adjacent to the distal-end tip on radially inner side thereof, the resin member, which is pressed outward, is caught between the distal-end tip and the wires, and thus, it is possible to more reliably prevent the contact between the wires and the distal-end tip.

In addition, in the above-described aspect, the distal end of the resin member may be disposed farther on a proximal-end side than the distal end of the distal-end tip is.

In addition, in the above-described aspect, the distal end of the resin member may be positioned farther on a proximal-end side of the distal-end tip than the distal end of the distal-end tip is and farther on a distal-end side of the distal-end tip than the proximal ends of the clearance grooves are.

In addition, in the above-described aspect, the resin member may be formed in a tubular shape, and the resin member may be positioned between the wires and the proximal ends of the clearance grooves in a state in which the wires are inserted into the clearance grooves.

In addition, in the above-described aspect, the resin member may be formed in a tubular shape attached to at least a portion of the inner circumferential surface or the outer circumferential surface of the distal-end tip.

With this configuration, it is possible to realize a resin member that overlaps with at least the proximal-end sides of the clearance grooves with a simple shape.

In addition, in the above-described aspect, the sheath may be a coil sheath in which a strand is wound in a coil shape, and the resin member may be attached to an inner circumferential surface or an outer circumferential surface of the coil sheath.

With this configuration, it is possible to utilize the distal-end portion of the resin member, which is mounted on the inner circumferential surface or the outer circumferential surface of the coil sheath, to prevent the contact between the wires and the distal-end tip. In the case in which the resin member is disposed on the inner-circumferential-surface side of the coil sheath, it is possible to make the resin member serve as a liner that reduces a sliding friction of the operating wire with respect to the coil sheath. In the case in which the resin member is disposed on the outer-circumferential-surface side of the coil sheath, it is possible to make the resin member serve as a cladding that covers the coil sheath.

In addition, in the above-described aspect, the gripping portion may be a basket wire.

In addition, in the above-described aspect, the gripping portion may be a snare.

In addition, in the above-described aspect, the wires of the gripping portion may be kept in a state in which the wires are in contact with the resin member when the operating wire is pulled toward a proximal end with respect to the sheath in a state in which the wires are disposed at positions at which the wires are inserted into the clearance grooves.

REFERENCE SIGNS LIST 1 endoscope treatment tool
4 sheath
5 operating wire
6 basket wire (gripping portion)
7 distal-end tip
8 tube (resin member)
9 wire
11 clearance groove
20 snare (gripping portion)

The invention claimed is:
1. An endoscope treatment tool comprising:
a tubular sheath having a longitudinal axis;
an operating wire disposed in an interior of the sheath, the operating wire being movable along the longitudinal axis;

a gripping portion provided at a distal end of the operating wire, the gripping portion having one or more wires for gripping a calculus;

a cylindrical metal distal-end tip attached to a distal end of the sheath, the distal-end tip having clearance grooves, each of the clearance grooves:

extending longitudinally from a distal end of the distal-end tip towards a proximal end of the distal-end tip, extending radially from an outer circumferential surface of the distal-end tip to an inner circumferential surface of the distal-end tip, and having a width at least as wide as a diameter of the one or more wires; and a resin member secured to the distal-end tip on a radially inner side or outer side thereof such that a distal end of the resin member extends distally past a proximal end of the clearance grooves.

2. The endoscope treatment tool according to claim 1, wherein the resin member is disposed radially inside the distal-end tip.

3. The endoscope treatment tool according to claim 2, wherein the distal end of the resin member is secured between the distal end of the distal-end tip and the proximal end of the clearance grooves.

4. The endoscope treatment tool according to claim 2, wherein the resin member is formed in a tubular shape, and the distal end of the resin member is positioned between the one or more wires and the proximal ends of the clearance grooves in a state in which the one or more wires are inserted into the clearance grooves.

5. The endoscope treatment tool according to claim 1, wherein the resin member is formed in a tubular shape and the resin member is secured to at least a portion of the inner circumferential surface or the outer circumferential surface of the distal-end tip.

6. The endoscope treatment tool according to claim 5, wherein the sheath is a coil sheath in which a strand is wound in a coil shape, and the resin member is secured to an inner circumferential surface or an outer circumferential surface of the coil sheath.

7. The endoscope treatment tool according to claim 1, wherein the gripping portion is a basket wire.

8. The endoscope treatment tool according to claim 1, wherein the gripping portion is a snare.

9. The endoscope treatment tool according to claim 1, wherein the one or more wires of the gripping portion are kept in a state in which the one or more wires are in contact with the resin member when the operating wire is pulled toward a proximal end with respect to the sheath in a state in which the one or more wires are disposed at positions at which the one or more wires are inserted into the clearance grooves.

10. The endoscope treatment tool according to claim 1, wherein the distal end of the resin member having a wire notch corresponding to a circumferential position of each of the clearance grooves, and a width of the wire notch is smaller than the width of the clearance grooves.

11. An endoscope treatment tool comprising:
a tubular sheath having a longitudinal axis;
an operating wire disposed in an interior of the sheath, the operating wire being movable along the longitudinal axis;
a gripping portion provided at a distal end of the operating wire, the gripping portion having one or more wires for gripping a calculus; and
the sheath having clearance grooves, each of the clearance grooves:
extending longitudinally from a distal end of the sheath towards a proximal end of the sheath,
extending radially from an outer circumferential surface of the sheath to an inner circumferential surface of the sheath, and,
having a width at least as wide as a diameter of the one or more wires, and
a resin member disposed at a position adjacent to the sheath on a radially inner side or outer side thereof, and
wherein a distal end of the resin member is disposed farther proximally than the distal end of the sheath; and
the distal end of the resin member having a wire notch corresponding to a circumferential position of each of the clearance grooves.

12. The endoscope treatment tool accoring to claim 11, wherein the resin member is secured to the distal-end tip on a radially inner side or outer side thereof such that at least a portion of the clearance grooves overlap longitudinally with the resin member.

13. The endoscope treatment tool according to claim 12, wherein the resin member is formed in a tubular shape, the distal end of the resin member is positioned between the one or more wires and the proximal ends of the clearance grooves in a state in which the one or more wires are inserted into the clearance grooves.

14. The endoscope treatment tool according to claim 11, wherein the resin member is formed in a tubular shape and the resin member is secured to at least a portion of the inner circumferential surface or the outer circumferential surface of the sheath.

15. The endoscope treatment tool according to claim 11, wherein the sheath is a coil sheath in which a strand is wound in a coil shape, and the resin member is secured to an inner circumferential surface or an outer circumferential surface of the coil sheath.

16. The endoscope treatment tool according to claim 11, wherein the gripping portion is a basket wire.

17. The endoscope treatment tool according to claim 11, wherein the one or more wires of the gripping portion are kept in a state in which the one or more wires are in contact with the resin member when the operating wire is pulled toward a proximal end with respect to the sheath in a state in which the one or more wires are disposed at positions at which the one or more wires are inserted into the clearance grooves.

18. The endoscope treatment tool according to claim 11, wherein a width of the wire groove is wider than a diameter of the one or more wires.

* * * * *